(12) United States Patent
Kim

(10) Patent No.: US 7,060,464 B2
(45) Date of Patent: Jun. 13, 2006

(54) PEPTIDES CONFERRING ENVIRONMENTAL STRESS RESISTANCE AND FUSION PROTEINS INCLUDING SAID PEPTIDES

(75) Inventor: Jong-Sun Kim, Seoul (KR)

(73) Assignee: Atgen Co., Ltd., Seoul (KR)

( * ) Notice: Subject to any disclaimer, the term of this patent is extended or adjusted under 35 U.S.C. 154(b) by 294 days.

(21) Appl. No.: 10/713,851

(22) Filed: Nov. 14, 2003

(65) Prior Publication Data

US 2005/0187378 A1    Aug. 25, 2005

Related U.S. Application Data

(62) Division of application No. 10/223,978, filed on Aug. 20, 2002, now Pat. No. 6,858,704.

(30) Foreign Application Priority Data

Nov. 20, 2001    (KR) .................. 10-2001-0072486

(51) Int. Cl.
*C12P 21/02*    (2006.01)
*C12N 1/21*    (2006.01)
*C12N 15/63*    (2006.01)
*C07H 21/04*    (2006.01)

(52) U.S. Cl. ............. 435/69.1; 435/252.3; 435/254.11; 435/320.1; 435/325; 536/23.5

(58) Field of Classification Search .................. None
See application file for complete search history.

(56) References Cited

U.S. PATENT DOCUMENTS

2002/0048763 A1*    4/2002    Penn et al. .................. 435/6

OTHER PUBLICATIONS

Kanda et al., "Enhanced Vulnerability to Oxidative Stress by alpha-synuclein☐☐Mutations and C-Terminal Truncation," Neuroscience, 2000, 97(2):279-284.*
Kim et al., "Structural Changes in alpha-synuclein Affect its Chaperone-like☐☐Activity in vitro," Protein Science, 2000, 9:2489-2496.*
Kim et al., "Thermal Behavior of Proteins: Heat-Resistant Proteins and Their Heat-☐☐Induced Secondary Structural Changes," Biochemistry, 2000, 39:14839-14846.*
Souza et al., "Chaperone-like Activity of Synucleins," FEBS Letters, 2000, 474:116-119.*

* cited by examiner

Primary Examiner—Robert A. Wax
(74) Attorney, Agent, or Firm—Joseph Hyosuk Kim; JHK Law

(57) ABSTRACT

The present invention relates to peptides comprising at least one sequence selected from the group consisting of oligopeptide sequences of at least about 10 but not more than about 50 continuous amino acid residues in the amino acid sequence of the C-terminal acidic tail (ATS), which can render fusion partner proteins environmental stress resistant by binding thereto while conserving their intrinsic properties. Also, it relates to fusion proteins formed by binding the above peptides to fusion partner proteins, nucleotide sequences encoding said fusion proteins, recombinant vectors comprising said nucleotide sequences, and cells transformed or transfected with said recombinant vectors. In addition, it relates to processes for producing the above environmental stress resistance conferring peptides or environmental stress resistant fusion proteins by chemical synthesis or genetic recombination.

14 Claims, 27 Drawing Sheets

FIG. 12A

GST-E5 ▬▬▬▬-EEEEE  (SEQ ID NO:36)

GST-E10 ▬▬▬▬-EEEEEEEEEE  (SEQ ID NO:37)

US 7,060,464 B2

PEPTIDES CONFERRING ENVIRONMENTAL STRESS RESISTANCE AND FUSION PROTEINS INCLUDING SAID PEPTIDES

RELATED APPLICATION

The present application is a divisional application of U.S. application Ser. No. 10/223,978, filed Aug. 20, 2002 now U.S. Pat. No. 6,858,704, which claims priority to Korean Application 10-2001-0072486, filed Nov. 20, 2001.

FIELD OF THE INVENTION

The present invention relates to novel peptides conferring environmental stress resistance to target proteins and to fusion proteins including the same peptides. More particularly, the present invention relates to peptides conferring environmental stress resistance comprising the C-terminal acidic tail of synuclein family (ATS) or peptides conferring environmental stress resistance comprising at least one sequence selected from the group consisting of oligopeptide sequences of at least about 10 but not more than about 50 continuous amino acid residues in the amino acid sequence of the ATS, to fusion proteins with environmental stress resistance formed by fusing said peptides with fusion partner proteins, to nucleotide sequences encoding said peptides and fusion proteins, to recombinant vectors comprising said nucleotide sequences, and to transformed or transfected cells with said recombinant vectors.

BACKGROUND OF THE INVENTION

"Proteins with environmental stress resistance" refer to proteins that physically, chemically and biologically show stability against external environmental factors such as heat, pH, metal ions, organic solvents, etc. Typically among such proteins, there are heat-stable proteins which are stable even at the boiling temperature of water. One group of heat-stable proteins is represented by proteins derived from hyperthermophilic organisms [Jaenicke R. and Bohm G., Curr. Opin. Struct. Bio., 8, 738–748 (1998); Ress D. C. and Adams M. W. W. Structure, 3, 251–254 (1995); and Adams M. W. W., Ann. Rev. Microbiol. 47, 627–658 (1993)]. These proteins have an extremely high melting temperature (hereinafter referred to as "Tm"), relative to their mesophilic counterparts (near or above the boiling point of water). However, when the temperature is increased above the Tm, most hyperthermophilic proteins also denature, leading to insoluble aggregation [Klump et al., J. Biol. Chem., 267, 22681–22685 (1992); Klump et al., Pure. Appl. Chem., 66, 485–489 (1994); Cavagnero S. et al., Biochemistry, 34, 9865–9873 (1995)].

Another group of heat-stable proteins, which has been recently recognized, is the intrinsically unstructured proteins [Plaxco, K. W. and Groβ M., Nature, 386, 657–658 (1997); Wright P. E. and Dyson H. J., J. Mol. Biol., 293, 321–331 (1999)]. The reason why the intrinsically unstructured proteins are heat-stable is because the conformation of the intrinsically unstructured proteins is not extensively changed by heat treatment. Thermodynamically, the intrinsically unstructured proteins are heat resistant proteins (hereinafter referred to as "HRPs") rather than heat-stable proteins since their conformation almost unfolds at room temperature and is somewhat changed at high temperatures (Kim T. D. et al., Biochemistry, 39, 14839–14846 (2000)). Thus, the term "heat resistant proteins (HRPs)" is more appropriate for describing the thermal behavior of the intrinsically unstructured proteins. That is, HRPs can be defined as proteins that are not aggregated by heat treatment, such as hyperthermophilic proteins and unstructured proteins.

The thermal behavior of proteins was systematically investigated by purifying and characterizing some HRPs that are not aggregated by heat treatment from Jurkat T cells and human serum (Kim T. D. et al., Biochemistry, 39, 14839–14846 (2000)). According to studies on the heat resistance of proteins from Jurkat cell lysates and human serum, four major types of thermal behavior of HRPs were recognized, which are as follows. Group I HRPs are represented by unstructured proteins such as α-synuclein and $α_s$-casein, which have a semi-unfolded conformation regardless of temperature. Group II HRPs, represented by human serum fetuin and albumin, are characterized by an irreversible conformational change upon heat treatment. Group III HRPs, represented by transthyretin and bovine serum fetuin, are characterized by a reversible conformational change. Group IV HRPs, conventional heat-stable proteins such as hyperthermophilic proteins, are characterized by the absence of heat induced conformational changes.

Most proteins unfold and in turn precipitate as the temperature increases, and the process is usually irreversible (Bull H. B. and Breese K., Arch. Biochem. Biophys., 156, 604–612 (1973)). The improvement of stress resistance, including the improvement of thermal stability, is one of the tasks to be solved for proteins, such as hormones, cytokines and enzymes, widely used in the medical or industrial fields. Improvement of stress-resistance, of course, renders the life span of products to be elongated, thereby leading to development of novel medical products and more stable industrial enzymes, foods or chemical products. Therefore, the present invention relating to novel stress-resistant proteins will be very useful.

SUMMARY OF THE INVENTION

In the study on properties of proteins against environmental stress such as heat, pH, metal ions, etc., the present inventors have discovered that peptides comprising the C-terminal acidic tail of the synuclein family (hereinafter referred to as "ATS") play a crucial role in providing environmental stress resistance. And fusion proteins prepared by fusing the ATS to target proteins (fusion partner proteins) show environmental stress resistance while conserving intrinsic properties of the proteins before fusion. Based on such findings, the present inventors have prepared such environmental stress resistant fusion proteins by chemical synthesis or genetic recombination, and thus completed this invention.

Therefore, the present invention provides peptides comprising the ATS, which can bind to fusion partner proteins and render them resistant to environmental stress while conserving their intrinsic properties.

In a further aspect, the present invention provides peptides comprising one sequence selected from the group consisting of oligopeptide sequences of at least about 10 but not more than about 50 continuous amino acid residues in the amino acid sequence of the ATS, which can render fusion partner proteins resistant to environmental stress by binding thereto while conserving their intrinsic properties.

In another aspect, the present invention provides fusion proteins with improved environmental stress resistance formed by binding peptides comprising at least one sequence selected from the group consisting of oligopeptide sequences of at least about 10 but not more than about 50 continuous amino acid residues in the amino acid sequence of the ATS to fusion partner proteins.

In another aspect, the present invention provides methods for preparing peptides comprising the ATS or peptides comprising at least one sequence selected from the group consisting of oligopeptide sequences of at least about 10 but not more than about 50 continuous amino acid residues in the amino acid sequence of the ATS.

In another aspect, the present invention provides methods for preparing fusion proteins with environmental stress resistance formed by binding peptides comprising at least one sequence selected from the group consisting of oligopeptide sequences of at least about 10 but not more than about 50 continuous amino acid residues in the amino acid sequence of the ATS to fusion partner proteins, by chemical synthesis or genetic recombination.

In another aspect, the present invention provides nucleotide sequences encoding peptides comprising the ATS or peptides comprising at least one sequence selected from the group consisting of oligopeptide sequences of at least about 10 but not more than about 50 continuous amino acid residues in the amino acid sequence of the ATS.

In another aspect, the present invention provides nucleotide sequences encoding peptides or fusion proteins with environmental stress resistance formed by binding peptides to fusion partner proteins, said peptides comprising at least one sequence selected from the group consisting of oligopeptide sequences of at least about 10 but not more than about 50 continuous amino acid residues in the amino acid sequence of the ATS.

In another aspect, the present invention provides primers to detect DNAs encoding fusion proteins with environmental stress resistance.

In another aspect, the present invention provides recombinant vectors containing the nucleotide sequences encoding the peptides or the fusion proteins with improved environmental stress resistance, said peptides comprising at least one sequence selected from the group consisting of oligopeptide sequences of at least about 10 but not more than about 50 continuous amino acid residues in the amino acid sequence of the ATS.

In yet another aspect, the present invention provides cells transformed or transfected with the recombinant vectors containing the nucleotide sequences encoding the peptides or the fusion proteins with improved environmental stress resistance, said peptides comprising at least one sequence selected from the group consisting of oligopeptide sequences of at least about 10 but not more than about 50 continuous amino acid residues in the amino acid sequence of the ATS.

BRIEF DESCRIPTION OF THE DRAWING

The above and other objects, features and other advantages of the present invention will be more clearly understood from the following detailed description taken in conjunction with the accompanying drawings, in which:

FIG. 12A is a schematic diagram of the GST-polyglutamate fusion proteins containing the polyglutamate tail (GST-E5 and GST-E10);

DETAILED DESCRIPTION OF THE INVENTION

Figure 1A:
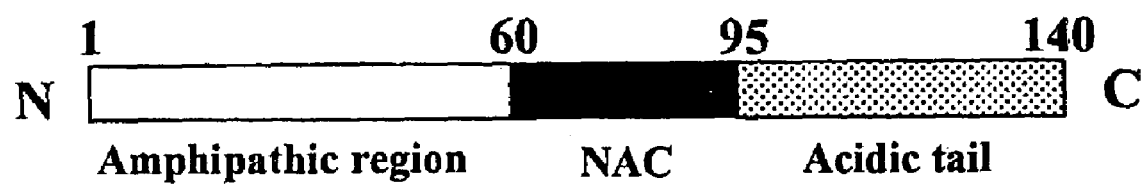
FIG. 1A is a schematic diagram of α-synuclein composed of the N-terminal amphipathic region (residues 1–60), the hydrophobic NAC region (residues 61–95) and the C-terminal acidic tail (residues 96–140)

The present invention provides peptides comprising the ATS, which can bind to fusion partner proteins and render them resistant to environmental stress while conserving their intrinsic properties. Also, the present invention provides peptides comprising at least one sequence selected from the group consisting of oligopeptide sequences of at least about 10 but not more than about 50 continuous amino acid residues in the amino acid sequence of the ATS.

The term "environmental stresses", as used herein, refers to physical or chemical actions which may cause denaturation of natural or non-natural proteins. In connection with this, the "denaturation of protein" means that a high order structure of a protein is changed by physical actions such as heating, freezing and drying, or chemical actions such as acids, alkalis, metal ions or organic solvents, generally including phenomena accompanying loss of biological functions, reduction in solubility, decrease or increase in reactivity, ease of decomposition by enzyme, loss of crystallinity, change of physicochemical properties, modified blue shift, etc. Examples of the environmental stresses which may denature the proteins in the present invention include physical factors such as temperature, moisture, pH, electrolyte, reduced sugar, pressurizing, drying, freezing, interfacial tension, light beam, etc. and chemical factors such as acids, alkalis, neutralized salts, organic solvents, metal ions, oxidizing/reducing agents, etc.

Specifically, the environmental stresses according to the present invention include temperature, moisture, pH, metal ions, electrolytes and oxidizing/reducing agents which may denature proteins. Most of proteins begin to denature at a temperature between 60 to 70° C. and the denaturation rate increases as the temperature rises. For example, when the temperature rises 10° C., the denaturation rates of albumin and hemoglobin increase 20 times and 13 times, respectively. However, when the temperature is sharply raised, the aggregation temperature may go up. When proteins thermally denature, water is needed. Water helps movement of polypeptide chains upon unfolding or recombining. Thus, if water is sufficient, thermal denaturation may take place at a lower temperature. Thermal denaturation of protein is also associated with pH and generally, at an acidic pH near pI the denaturation occurs faster. Using such property, when cooking fish, a small amount of vinegar is added to rapidly harden the fresh fish. Further, the denaturation of proteins may be induced by addition of electrolytes (salts). Upon addition of the electrolyte, cations in the electrolyte such as salt compounds, sulfates may neutralize negative charges of a protein, rendering pH to be pI. If reduced sugar is present when applying heat to a protein, Maillard reaction, non-enzymatic browning, occurs to destroy essential amino acids.

Among the environmental stresses according to the present invention, are included pressurizing and dry circumstances which may cause denaturation of proteins. In general, proteins are denatured by application of a high pressure in the range of 5000 to 10000 atm or by sonication. Particularly, soluble proteins may be denatured by drying. As drying progresses, moisture existing between polypeptide chains disappears, upon which adjacent peptide chains are recombined to form a more solid structure.

Among the environmental stresses according to the present invention, are included freezing circumstances which may cause denaturation of proteins. For example, when meat is frozen, water is first crystallized as ice crystals because of its weak bonding force. Consequently, salt concentration in the remaining liquid is increased, causing salting out, by which proteins are denatured. Among another environmental stresses, interfacial tension is included. Proteins are denatured upon spreading as a single molecular layer on the interface, resulting in aggregation. Further, among another environmental stresses, irradiation of light which may cause denaturation of protein is included. Upon irradiation of light to protein, bonds in the protein tertiary structure are broken, resulting in denaturation. Acids, alkalis, neutral salts, organic solvents such as alcohols or acetones and metal ions are included among the environmental stresses for the purpose of the present invention. When acid, alkali is added to protein solutions, (+) and (−) charges are changed, which in turn causes alteration of ionic bonds, which are intimately connected with the high order structure, thereby resulting in denaturation of proteins.

The "Synuclein family" is a group of heat-resistant proteins that are known not to aggregate by heat treatment, its known members including α-synuclein, β-synuclein, δ-synuclein and synoretin. The synucleins are proteins found in higher animals above fish and also have been reported to be present in humans, rat, bird, bovine, etc. [Clayton and Geroge, Trends in Neuroscience 21, 249–254 (1998)]. The peptides according to the present invention may preferably include ones derived from the C-terminal acidic tail of human origin α-, β-, and δ-synucleins.

The "C-terminal acidic tail (ATS)" may be those derived from the synuclein family, preferably SEQ ID NO:1 (derived from α-synuclein), SEQ ID NO:2 (derived from β-synuclein), SEQ ID NO:3 (derived from γ-synuclein) and SEQ ID NO:4 (derived rom synoretin). The term "C-terminal acidic tail of synuclein family" is abbreviated to "ATS" for simplicity and clarity of description. More specifically, "the C-terminal acidic tail of α-synuclein (amino acid residues 96–140)" is abbreviated to "ATSα" or "Sn96–140"; "the C-terminal acidic tail of β-synuclein (amino acid residues 85–134)" is abbreviated to "ATSβ" or Syn85–134; "the C-terminal acidic tail of γ-synuclein (amino acid residues 96–127)" is abbreviated to "ATSγ" or Syn96–127.

Particularly, α-synuclein, which is an acidic presynaptic protein of 140 amino acids (Ueda K. et al., Proc. Natl. Acad. Sci. USA, 90, 11282–11286 (1993); Jakes R. et al., FEBS lett., 345, 27–32 (1994)), belongs to the intrinsically unstructured protein family (Eliezer D. et al., J. Mol. Biol. 307, 1061–1073 (2001); Kim J., Molecules and Cells, 7, 78–83 (1997); Weinreb P. H. et al., Biochemistry, 35, 13709–13715 (1996)).

Since α-synuclein is intrinsically unstructured in its native state, it may interact with many other proteins or ligands (Kim J., Molecules and Cells, 7, 78–83 (1997); Weinreb P. H. et al., Biochemistry, 35, 13709–13715 (1996)). α-synuclein acquires an increased level of secondary structure, when it associates with small acidic phospholipid vesicles, detergents, organic solvents and some metal ions (Eliezer D. et al., J. Mol. Biol., 307, 1061–1073 (2001); Kim T. D. et al., Protein Science, 9, 2489–2496 (2000); Davidson W. S. et al., J. Biol. Chem., 273–9443–9 (1998); Weinreb P. H. et al., Biochemistry, 35, 13709–13715 (1996); Paik S. R. et al., Biochem. J., 340, 821–8 (1999)). As mentioned above, α-synuclein is extremely heat resistant, which is possibly due to the abnormal primary and tertiary structure features.

As shown in FIG. 1, α-synuclein consists of three distinct regions: the amino-terminal amphipathic region (residues 1–60), the hydrophobic NAC region (residues 61–95) and the carboxy-terminal acidic tail (residues 96–140) [Lucking C. B. and Brice A. Cell. Mol. Life Sci., 57, 1894–1908 (2000); Iwai A. Biochim. Biophys. Acta. 1502, 95–109 (2000); Hashimoto M. and Masliah E., Brain Pathol., 9, 707–720 (1999); Lavedan C. Genome Res., 8, 871–880 (1998)]. The N-terminal region is highly conserved between species, while the C-terminal acidic tail region is highly variable in size as well as in sequence. The C-terminal acidic tail of synuclein family (ATS) is highly variable in size and sequence [Lucking C. B. and Brice A. Cell. Mol. Life Sci., 57, 1894–1908 (2000); Iwai A. Biochim. Biophys. Acta. 1502, 95–109 (2000); Hashimoto M. and Masliah E., Brain Pathol., 9, 707–720 (1999); Lavedan C. Genome Res., 8, 871–880 (1998)]. In contrast, the N-terminal amphipathic region is highly conserved between species, among the synuclein family members from the Torpedo to humans.

Also, the present invention embraces fusion proteins with improved environmental stress resistance formed by binding peptides, comprising the ATS or peptides comprising at least one sequence selected from the group consisting of oligopeptide sequences of at least about 10 but not more than about 50 continuous amino acid residues in the amino acid sequence of the ATS and conferring environmental stress resistance, to fusion partner proteins.

The "fusion partner protein" refers to any proteins which is preferred to have increased resistance to environmental stresses, particularly, proteins which are environmental stress-labile in themselves. The term "environmental stress-labile proteins" refers to proteins that are easily denatured by environmental stresses. The "denaturation" means the same as defined above. The environmental stress-labile proteins are well-known according to the denaturing factors.

The fusion partner proteins, to which the peptides according to the present invention bind, can bind with either the N-terminus or C-terminus, or simultaneously with both the N-terminus and the C-terminus. The fusion partner proteins can be derived from one protein or two or more different proteins.

The environmental stress-resistant fusion proteins according to the present invention include any fusion proteins formed by binding peptides of the ATS or peptides comprising at least one sequence selected from the group consisting of oligopeptide sequences of at least about 10 but not more than about 50 continuous amino acid residues in the amino acid sequence of the ATS and conferring environmental stress resistance, to fusion partner proteins, as long as the peptides do not affect the intrinsic properties of the fusion proteins, regardless of the binding sites.

As a group, the environmental stress-resistant fusion proteins according to the present invention embraces fusion proteins with improved environmental stress resistance formed of peptides of the ATS or peptides with environmental stress resistance comprising at least one sequence selected from the group consisting of oligopeptide sequences of at least about 10 but not more than about 50 continuous amino acid residues in the amino acid sequence of the ATS, fused to the N-terminus of fusion partner proteins.

As another group, the environmental stress-resistant fusion proteins according to the present invention embraces fusion proteins with improved environmental stress resistance formed of peptides of the ATS or peptides with environmental stress resistance comprising at least one sequence selected from the group consisting of oligopeptide sequences of at least about 10 but not more than about 50 continuous amino acid residues in the amino acid sequence of the ATS, fused to the C-terminus of fusion partner proteins.

As a preferred group, the environmental stress-resistant fusion proteins according to the present invention are preferably fusion proteins formed of the NAC region and ATSα region, or the NAC-region and peptides with environmental stress resistance comprising at least one sequence selected from the group consisting of oligopeptide sequences of at least about 10 but not more than about 50 continuous amino acid residues in the amino acid sequence of the ATSα, fused to the N-terminus of proteins which are known to be unstable to environmental stresses.

As another preferred group, the environmental stress-resistant fusion proteins according to the present invention are preferably fusion proteins formed of the full-length α-synuclein fused to the C-terminus of proteins which are known to be unstable to environmental stresses.

As another preferred group, the environmental stress-resistant fusion proteins according to the present invention are preferably fusion proteins formed of the full-length α-synuclein fused to the N-terminus of proteins which are known to be unstable to environmental stresses.

As another preferred group, the environmental stress-resistant fusion proteins according to the present invention are preferably fusion proteins formed of the NAC region and ATSα region, or the NAC-region and peptides with environmental stress resistance comprising at least one sequence selected from the group consisting of oligopeptide sequences of at least about 10 but not more than about 50 continuous amino acid residues in the amino acid sequence of the ATSα, fused to the C-terminus of proteins which are known to be unstable to environmental stresses.

The fusion proteins of the present invention may form numerous forms of proteins according to the binding site to which the ATS or at least about 10 but not more than about 50 amino acid sequences of the ATS bind, and kinds and numbers of the fusion partner proteins.

In an embodiment of the present invention, as the fusion partner proteins, glutathione S-transferase and dihydrofolate reductase, hereinafter referred to as "GST" and "DHFR", respectively, which are known to be environmental stress-labile, may be used. Another examples of the fusion partner proteins include α-synuclein except for the ATSα, and the NAC of α-synuclein.

GST, which is used by an example in the present invention, exists generally in bacteria to mammal and functions to detoxify various cytotoxins in vivo, or participate in protecting cells from oxidation damage, or transporting a variety of hydrophobic and amphipathic substances including lipids, bilirubin, ham, steroid, bile salts, etc. Also, it is found in various cancer cells or drug-resistance cells, used as a target molecule or tumor marker molecule in chemotherapy and applied for diagnosis. GST and DHFR are known to be heat-labile proteins that readily precipitate by heat stress. In the present invention, it was confirmed that GST and DHFR aggregate and precipitate by heat treatment through qualitative analysis using SDS-polyacrylamide gel after heat treatment and thus found GST and DHFR are very heat-labile proteins.

Also, the human origin α-synuclein which is used as an example, does not precipitate in the experiment to examine its thermostability, even when it is placed in boiling water (about 100° C.), and thus found to have heat resistance. Furthermore, in the experiment to examine thermostability of a series of deletion mutants prepared by enzymatically decomposing the α-synuclein protein, it was shown that the ATSα region (residues 96–140, Syn96–140) plays a critical role in conferring the heat-resistance to the synuclein protein (Example 4).

In the present invention, based on the heat-resistance of the ATSα, fusion proteins are constructed by binding peptides containing the ATSα to the C-terminal of the heat-labile GST. For example, a fusion protein formed by binding the ATSα to the C-terminal of GST, represented by SEQ ID NO:5, a fusion protein formed by binding the peptide (amino acid residues 61–140) composed of the NAC region and the acidic tail region of α-synuclein to the C-terminal of GST, represented by SEQ ID NO:6, and a fusion protein formed by binding the full-length peptide (amino acid residues 1–140) of α-synuclein to the C-terminal of GST, represented by SEQ ID NO:7 are constructed. These fusion proteins are found not to aggregate even when heat treated at 100° C. for 30 minutes. Also, fusion proteins with α-synuclein peptides lacking the acidic tail region linked to the C-terminal of the heat-labile GST are constructed. For example, a fusion protein formed by binding the peptide of the NAC region of α-synuclein to the C-terminal of GST, and a fusion protein formed by binding the peptide of the amphipathic region of α-synuclein to the C-terminal of GST are constructed. These fusion proteins are found to aggregate and precipitate when heat treated at 100° C. for 30 minutes. From the foregoing results, it is demonstrated that the ATSα (Syn96–140) plays a critical role in conferring heat-resistance to GST (Example 5). Also, it is demonstrated that the ATSα can effectively prevent aggregation of GST induced by pH or metal ions (Example 10). Therefore, it is presumed that the ATSα has a property to confer environmental stress resistance to fusion partner protein.

In the present invention, based on the fact that introduction of the C-terminal acidic tail of α-synuclein (ATSα) can confer heat-resistance to the produced GST-ATSα fusion proteins, in order to confirm whether the ATSα can confer heat-resistance to other proteins in addition to GST, DHFR-ATSα is constructed by introducing the ATSα to the C-terminus of DHFR. As a result, unlike wild-type DHFR, DHFR-ATSα is also found not to precipitate even when heat treated at 100° C. for 30 minutes. From this result, it is demonstrated that the ATSα is excellent in increasing stress resistance of DHFR and other stress-labile proteins in addition to GST (Example 11).

In the present invention, a series of GST-synuclein fusion proteins with peptide fragments derived from the ATSα were produced. These fusion proteins also appeared to be heat resistant. Among these fusion proteins, GST-Syn96–140 containing the entire region of ATSα and GST-Syn119–140 containing 22 amino acids of ATSα did not precipitate at all after heat treatment regardless of the concentration, while GST-Syn103–115, GST-Syn114–126 and GST-Syn130–140 containing 11–13 amino acids did not precipitate at all at a low concentration but increasingly aggregated as the concentration was raised. Thus, it is demonstrated that the deletion mutants of the GST-ATSα fusion protein have heat resistance superior to that of wild type GST and the heat resistance interestingly varies according to the length of ATSα (Example 12).

In the present invention, GST-ATSβ and GST-ATSγ fusion proteins containing the acidic tails of 3-synuclein (ATSβ) and γ-synuclein (ATSγ), respectively, were produced, and these fusion proteins were also found to be extremely heat resistant. Thus, it is demonstrated that in addition to ATSα, the ATSβ and ATSγ are peptides capable of providing heat resistance to other proteins and they can be used in preparation of fusion proteins having resistance to environmental stresses (Example 13).

In the present invention, the GST-polyglutamate fusion proteins were also prepared and compared for their heat resistance with those of GST-ATS fusion proteins. As a result, it is noted that the polyglutamate tail is considerably less effective to provide heat resistance, as compared with ATS peptides containing the same number of glutamate residues. For example, GST-Syn130–140 shows heat resistance far superior to GST-E5 containing the same number of glutamate residues and even slightly higher than that of GST-E10 containing two times more glutamate residues (Example 14). Therefore, it is suggested that the characteristic amino acid sequence of ATS, in addition to the increased solubility of proteins due to the increase of the negative charge, plays an important role in the mechanism, by which fusion proteins with ATS show high resistance to environmental stresses.

The fusion proteins prepared according to the present invention have heat-resistance that does not aggregate nor precipitate when heat treated at water boiling point of higher than 100° C. for several minutes (Example 5). The $T_{50}$ value of wild type GST and the fusion protein GST-Syn96–140 with the C-terminal acidic tail region (amino acid residues 96–140) of α-synuclein binding to the C-termini of GST are found to be 55.5° C. and 57.5° C., respectively, which indicates that the acidic tail region increases the thermostability of the fusion protein. Such a significant increase in thermostability observed from the GST-Syn96–140, results from the fact that the acidic tail protects the protein from heat-induced aggregation. Also, as shown in FIG. 6B, GST aggregates from 52° C., which is much lower than the melting point (70° C.), whereas the GST-Syn96–140 fusion protein does not.

According to the present invention, it was shown that the ATSα plays a critical role in conferring heat-resistance to heat-labile proteins as well as to the synuclein protein itself. The ATSα may cause unfavorable intermolecular interaction by repulsion between negatively charged residues. This idea is supported by the observation that α-synuclein mutants with a truncated C-terminal acidic tail and the NAC peptide lacking the C-terminal acidic tail aggregates faster than the full-length α-synuclein under the same conditions (Sperpell L. C. et al., Proc. Natl. Acad. Sci. USA, 97, 4897–4902 (2000); Crowther R. A. et al., FEBS Letters, 436, 309–312 (1998); Han H. et al., Chem. Biol., 2, 163–169 (1995); Iwai A. et al., Biochemistry, 34, 10139–10145 (1995)). Therefore, the ATSα may increase the hydrophilicity and thereby, solubility of proteins or fusion proteins containing it and consequently inhibit heat-induced aggregation of the proteins or fusion proteins.

The heat-resistant fusion proteins, prepared according to the present invention, are characterized by low hydropathy and pI (isoelectric point) compared with heat-labile proteins (Example 6). The solubility of a protein is approximately proportional to the square of the net charge on the protein (Tanford C., John Wiley and Sons, Inc. New York (1961)). In fact, introducing the ATSα into heat-labile proteins significantly decreases the PI and hydropathy values of the resultant fusion proteins (Table 1).

The fusion proteins prepared according to the present invention are characterized by inhibiting decrease of enzymatic activity by heat. The GST-Syn96–140 fusion protein according to the present invention show a $T_{50}$ value higher than that of GST (Example 8).

The GST-Syn96–140 fusion protein prepared according to the present invention belong to Group II HRPs (Example 7). Upon examination of its structure using far-UV CD spectrum, the GST-Syn-96–140 fusion protein prepared according to the present invention was found to contain well-ordered secondary structural elements. The far-UV CD spectrum showed a decrease in these elements at 100° C. but the overall shape was unchanged. After cooling, the far-UV CD spectrum remains distinguishable from the initial one, which suggests that the conformation of the GST-Syn96–140 fusion protein may be irreversibly changed. The CD spectrum of the heat-treated GST-Syn96–140 at room temperature rather resembles that obtained at 100° C., which indicates that the protein consists of two distinct domains: one with regular secondary structural elements and the other with a random-coil like conformation (Example 9).

α-synuclein has the potential to bind several divalent and metal ions including $Fe^{2+}$, $Al^{3+}$, $Zn^{2+}$, $Cu^{2+}$ and $Ca^{2+}$ (Paik S. R. et al., Arch, Biochem. Biophys, 344, 325–334 (1997); Paik S. R. et al., Biochem. J., 340, 821–8 (1999); Nielsen M. S. et al., J. Biol. Chem., 276, 22680–22684 (2001)). Metal ions ($Fe^{2+}$, $Al^{3+}$, $Zn^{2+}$ and $Cu^{2+}$) bind to α-synuclein and induce self-oligomerization of the protein. $Cu^{2+}$ and $Ca^{2+}$ are known to specifically bind to the ATSα region with a dissociation constant of 59 μM and an $IC_{50}$ of 300 μM, respectively (Paik S. R. et al., Biochem. J., 340, 821–8 (1999); Nielsen M. S. et al., J. Biol. Chem., 276, 22680–22684 (2001)). However, the binding sites and binding constants of $Fe^{2+}$, $Al^{3+}$ and $Zn^{2+}$ have not yet to be determined.

The heat-resistant fusion proteins prepared according to the present invention does not aggregate by divalent cations and metal ions. The GST proteins fused with the ATSα according to the present invention show resistance to pH- and metal-induced aggregation and the ATSα protects fusion proteins from environmental stresses, thereby causing substantial increase in stability (Example 10). According to the present invention, it was shown that the divalent cation binding does not affect the thermal behavior of α-synuclein and the GST-α-synuclein fusion proteins.

Also, the present invention provides methods for preparing the ATS peptides or peptides containing at least one sequence selected from the group consisting of oligopeptide sequences of at least about 10 but not more than about 50 continuous amino acid residues in the amino acid sequence of the ATS by chemical synthesis or genetic recombination.

The peptides of the present invention which are to be fused to target proteins can be easily prepared by chemical synthesis widely known to those skilled in the field of biochemistry (Creighton, Proteins: Structures and Molecular Principles, W. H. Freeman and Co., NY (1983)). Representative methods include liquid or solid phase synthesis, fragment condensation, F-MOC or T-BOC chemistry [Chemical Approaches to the Synthesis of Peptides and Proteins, Williams et al., Eds., CRC Press, Boca Raton Fla., (1997); A Practical Approach, Atherton & Sheppard, Eds., IRL Press, Oxford, England (1989)].

The peptides according to the present invention can be synthesized by performing the condensation reaction between protected amino acids by the conventional solid-phase method, beginning with the C-terminal and progressing sequentially with the first amino acid, the second amino acid, the third amino acid, and the like. After the condensation reaction, the protecting groups and the carrier connected with the C-terminal amino acid may be removed by a known method such as acid decomposition or aminolysis. The above-described peptide synthesis method is described in detail in literature [Gross and Meienhofer's, The peptides, vol 2., Academic Press (1980)].

The solid-phase carrier, which can be used in the synthesis of the peptides according to the present invention, includes polystyrene resins of substituted benzyl type, polystyrene resins of hydroxymethylphenylacetic amid form, substituted benzhydrylpolystyrene resins and polyacrylamide resins, having a functional group capable of bonding to peptides.

The protecting groups for initial protected amino acids are any protecting groups commonly used in peptide syntheses, including those readily removable by conventional methods such as acid decomposition, reduction or aminolysis. Specific examples of such amino protecting groups include formyl; trifluoroacetyl; benzyloxycarbonyl; substituted benzyloxycarbonyl such as (ortho- para-)chlorobenzyloxycarbonyl and (ortho- para-)bromobenzyloxycarbonyl; and aliphatic oxycarbonyl such as t-butoxycarbonyl and t-amiloxycarbonyl. The carboxyl groups of amino acids can be protected through conversion into ester groups. The ester groups include benzyl esters, substituted benzyl esters such as methoxybenzyl ester; alkyl esters such as cyclohexyl ester, cycloheptyl ester or t-butyl ester. The guanidino residue may be protected by nitro; or arylsulfonyl such as tosyl, methoxybenzensulfonyl or mesitylenesulfonyl, though it does not need a protecting group. The indole group of tryptophan may be protected by formyl or may not be protected.

Removal of protecting groups and carriers from peptides can be carried out using anhydrous hydrofluoride in the presence of various scavengers. Examples of the scavengers include those commonly used in peptide syntheses such as anisole, (ortho-, metha-, para-)cresol, dimethylsulfide, Co-cresol, ethanendiol and mercaptopyridine.

In other means, the peptides according to the present invention can be prepared by genetic engineering methods. Firstly, DNA sequences encoding the peptides are constructed according to conventional methods. The DNA sequences are constructed by PCR amplification using appropriate primers. Alternatively, the DNA sequences may be synthesized using any standard method known in the art, e.g., by use of an automated DNA synthesizer (such as are commercially available from Biosearch, Applied Biosystems, etc.). As examples, phosphorothioate oligonucleotides may be synthesized by the method of Stein et al. [Stein et al., 1988, Nucl. Acids Res. 16:3209 (1988)]. Methylphosphonate oligonucleotides can be prepared by use of controlled pore glass polymer supports [Sarin et al., 1988, Proc. Natl Acad. Sci. U.S.A. 85, 7448–7451 (1988)].

The constructed DNA sequences are inserted into vectors comprising one or more expression control sequences regulating expression of the DNA sequences to form recombinant expression vectors. Host cells are transformed or transfected with the vectors and the transformants or transfectants are cultured in a proper medium under proper conditions so that the DNA sequences express. By this way, substantially pure peptides encoded by the DAN sequences may be obtained from the cultures.

The term "transformation", as used herein, refers to a phenomenon that DNA becomes replicable in a form other than a chromosome or integration into a chromosome, when it is introduced into a vector. The term "transfection", as used herein, refers to a phenomenon that an expression vector is received by the host cells whether or not any coding sequence is expressed in practice.

The terms "transformed host cells" and "transfected host cells" refer to introduction of DNA into cells. The cells are so-called as "host cells", which may be eukaryotic or prokaryotic cells. Typical eukaryotic host cells include various strains of E. coli. Typical prokaryotic host cells include cells derived from mammals, for example, Chinese hamster ovary and human. The introduced DNA sequences may be obtained from species which is the same with or different from the host cells, or be a hybrid DNA sequence containing any heterologous or homologous DNA.

The term "vector", as used herein, refers to a DNA construct containing a DNA sequence which is operably linked to a control sequence capable of effecting the expression of the DNA in a suitable host cell. Such control sequences include a promoter to effect transcription, an optional operator sequence to control such transcription, a sequence encoding suitable mRNA ribosome binding sites, and sequences which control the termination of transcription and translation. The vector may be a plasmid, a virus, a phage particle, or simply a potential genomic insert. Once transformed into a suitable host, the vector may replicate and function independently of the host genome, or may, in some instances, integrate into the genome itself. In the present specification "plasmid" and "vector" are sometimes used interchangeably as the plasmid is the most commonly used form of vector at present. However, the invention is intended to include such other forms of vectors which serve equivalent functions and which are, or become, known in the art. Preferred expression vectors for mammalian cell culture expression are based on pRK5 (EP 307,247), pSVI6B (PCT Publication No WO 91/08291) and pVLI392 (Pharmingen).

The term "control sequence" refers to DNA sequences, which are necessary to affect the expression of coding sequence operably linked to specific host organisms. For example, control sequences suitable for eukaryotic organisms include promoters, any operator sequences and ribosomal binding sites. The prokaryotic organisms use promoters, polyadenylated signal and enhancers.

A nucleic acid is "operably linked" to another nucleic acid, when they are arranged in a functional relationship. This means that when an appropriate molecule (for example, a transcription activator) binds to a control sequence(s), a gene or a control sequence(s) is(are) linked in such a way that the expression of the gene is modulated. For example, DNA for a pre-sequence or secretory leader is operably linked to DNA for a polypeptide if it is expressed as a precursor, which participates in the secretion of the polypeptide; a promoter is operably linked to a coding sequence, if it affects the transcription of the sequence; or a ribosome binding site is operably linked to a coding sequence, if it is positioned so as to facilitate translation. Generally, the expression "operably linked" means contiguous and, in the case of secretory leaders, contiguous and in reading frame. However, the enhancer does not need to be contiguous. The linkage of these sequences are effected by ligation (linkage) in a convenient restriction enzyme site. If such a site does not exist, a conventionally synthesized oligonucleotide adaptor or linker may be used.

The term "expression vector", as used herein, refers to a recombinant carrier with a heterologous DNA fragment inserted, which is generally a double-stranded DNA fragment. Here, the heterologous DNA is defined as a foreign DNA, which is not naturally found in the host cell. The expression vector can be replicated regardless of the host chromosome DNA, once in the host cell to produce several copies of the vector and (heterologous) DNA with itself inserted.

As it is well known in the art, in order to increase expression levels of a transfected gene in a host, the gene must be operatively linked to transcriptional and translational expression control sequences that are functional in the selected expression host. Preferably, the expression control sequences, and the gene of interest, will be contained in an expression vector that further comprises a bacterial selection marker and origin of replication. If the expression host is a eukaryotic cell, the expression vector should further comprise an expression marker useful in the eukaryotic expression host.

Various expression host/vector combinations may be employed in expressing the DNA sequences of the present invention. Useful expression vectors for eukaryotic hosts include, for example, vectors comprising expression control sequences derived from SV40, bovine papilloma virus, adenovirus, adeno-associated virus, cytomegalovirus and retroviruses. Useful expression vectors for bacterial hosts include bacterial plasmids, such as those derived from E. coli, including pET, pRSET, pBluescript, pGEX2T, pUC vectors, col E1, pCR1, pBR322, pMB9 and derivatives thereof, wider host range plasmids, such as RP4, phage DNAs, for example, the numerous derivatives of phage lambda, for example λ GT10 and λ GT11, NM989, and other DNA phages, such as M13 and filamentous single stranded DNA phages. Useful expression vectors for yeast cells include the 2μ plasmid and derivatives thereof. Useful vectors for insect cells include pVL 941.

In addition, any of various expression control sequences may be used in these vectors to express the DNA sequences of this invention. Useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the T3 and T7 promoters the major operator and promoter regions of phage lambda, the control regions of fd coat protein, the promoter for 3-phosphoglycerate kinase or other glycolytic enzymes, the promoters of acid phosphatase, for example, Pho5, the promoters of the yeast alpha-mating system and other constitutive and inducible promoter sequences known to control the expression of genes of prokaryotic or eukaryotic cells or their viruses, and various combinations thereof. The T7 RNA polymerase promoter Φ 10 is particularly useful in the expression of the peptides in E. coli.

Host cells transformed or transfected with the foregoing vectors form a further aspect of the present invention. Various unicellular host cells are useful in expressing the DNA sequences of the present invention. These hosts may include well known eukaryotic and prokaryotic hosts, such as strains of E. coli, Pseudomonas, Bacillus, Streptomyces, fungi, yeast, insect cells such as Spodoptera frugiperda (SF9), animal cells such as CHO and mouse cells, African green monkey cells such as COS 1, COS 7, BSC 1, BSC 40, and BMT 10, human cells, and plant cells in tissue culture. Preferred host organisms include bacteria such as E. coli and B. subtilis, and mammalian cells in tissue culture.

It should of course be understood that not all vectors and expression control sequences will function equally well to express the DNA sequences of the present invention. Neither will all hosts function equally well with the same expression system. However, one skilled in the art may make an appropriate selection among these vectors, expression control sequences and hosts without undue experimentation and without departing from the scope of the present invention. For example, in selecting a vector, the host must be considered because the vector must replicate in it. The vector's copy number, the ability to control that copy number, and the expression of any other proteins encoded by the vector, such as antibiotic markers, should also be considered. In selecting an expression control sequence, a variety of factors should also be considered. These include, for example, the relative strength of the sequence, its controllability, and its compatibility with the DNA sequences of the present invention, particularly as regards to potential secondary structures. Unicellular hosts should be selected by consideration of their compatibility with the chosen vector, the toxicity of the product coded for by the DNA sequences of the present invention, their secretion characteristics, their ability to fold the protein correctly, their culture and fermentation requirements and the ease of purification from them of the products coded for by the DNA sequences of this invention. Within these parameters, one skilled in the art may select various vector/expression control sequence/host combinations that will express the DNA sequences of the present invention in large scale culture.

The peptides encoded by the DNA sequences of the present invention may be isolated from the fermentation or cell culture and purified using any of conventional methods including: liquid chromatography such as normal or reversed phase using HPLC, FPLC and the like; affinity chromatography (such as with inorganic ligands or monoclonal antibodies); size exclusion chromatography; immobilized metal chelate chromatography; gel electrophoresis and the like. One skilled in the art may select the most appropriate isolation and purification techniques without departing from the scope of the present invention. The term "substantially pure peptide" means that the polypeptides according to the present invention are substantially free from other proteins of bacterial origin.

Also, the present invention provides methods for preparing fusion proteins with environmental stress resistance according to the present invention by chemical synthesis or genetic recombination. Preferably, the fusion proteins with environmental stress resistance according to the present invention are prepared by genetic recombination, The skilled in the biochemistry and genetic engineering fields may appreciate that the preparation of the fusion proteins comprising peptides of the C-terminal acidic tail region of the synuclein family or at least one sequence selected from the group consisting of amino acid sequences of at least 10 but not more 50 amino acids in the amino acid sequence of the C-terminal acidic tail region of the synuclein family and proteins bound thereto is accomplished by using a conventional technology.

The present invention provides nucleotide sequences encoding the peptides comprising the C-terminal acidic tail region of the synuclein family. Also, the present invention provides nucleotide sequences encoding the peptides comprising at least one sequence selected from the group consisting of oligopeptide sequences of at least about 10 but not more than about 50 amino acids in the amino acid sequence of the C-terminal acidic tail region of the synuclein family and which can render fusion partner proteins environmental stress resistant by binding thereto while conserving their intrinsic properties. Further, the present invention provides nucleotide sequences encoding the fusion proteins with the peptides binding to fusion partner proteins.

In a particular embodiment, there are provided DNA sequences encoding amino acid sequences of fusion proteins having peptides of the C-terminal acidic tail region of α-synuclein binding to the C-termini of the heat-labile GST protein. For example, there are the DNA sequence (SEQ ID NO:8) encoding GST-Syn96–140, a fusion protein having the amino acid sequence of the C-terminal acidic tail region (amino acid residues 96–140) of α-synuclein binding to the C-termini of the amino acid sequence of GST, the DNA sequence (SEQ ID NO:9) encoding GST-Syn61–140, a fusion protein having the amino acid sequence containing the NAC region and the C-terminal acidic tail region (amino acid residues 96–140) of α-synuclein binding to the C-termini of the amino acid sequence of GST, or the DNA sequence (SEQ ID NO:10) encoding GST-Syn1–140, a fusion protein having the full-length amino acid sequence (amino acid residues 1–140) of α-synuclein binding to the C-termini of the amino acid sequence of GST.

The present invention provides primers to detect DNAs encoding the proteins with environmental stress resistance. In additional embodiment of the present invention, there is provided recombinant vectors containing the nucleotide sequences and cells transformed or transfected with the recombinant vectors.

Now, the present invention will be described in detail by the following examples. However, the examples are for illustration of the present invention and do not limit the scope of the present invention thereto.

EXAMPLES

Example 1

Figure 1B:
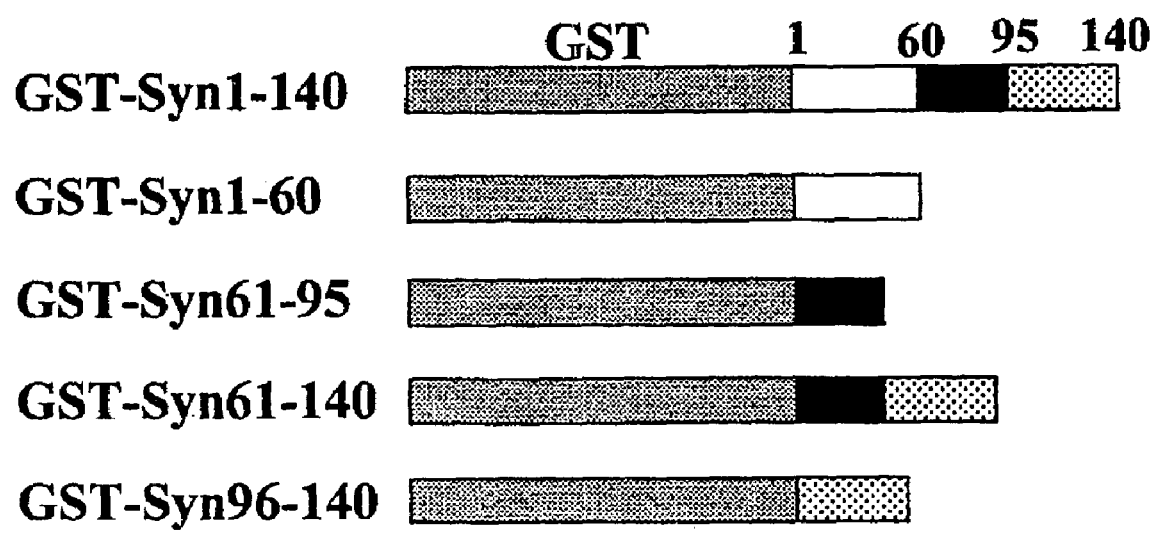
FIG. 1B is a schematic diagram of fusion proteins GST-Syn1–140, GST-Syn1–60, GST- Syn61–95, GST-Syn61–140 and GST-Syn96–140, which are formed by binding peptides of the full length α-synuclein, the amphipathic region, the NAC region, the NAC region and acidic tail regions, and the acidic tail region, respectively, to the C-terminus of glutathion S-transferase (GST), a heat-labile protein.

Preparation of GST-synuclein Fusion Constructs and Expression Vectors

α-synuclein consists of three distinct regions, the N-terminal amphipathic region (residues 1–60; FIG. 1A), the hydrophobic NAC region (residues 61–95; FIG. 1A), and the C-terminal acidic region (residues 96–140; FIG. 1A). Five GST-synuclein fusion constructs encoding GST- Syn1–140, a fusion protein of the entire region of α-synuclein and GST, GST-Syn1–60, a fusion protein of the amphipathic region and GST, GST-Syn61–95, a fusion protein of the NAC region and GST, GST-Syn61–140, a fusion protein of the NAC plus acidic tail region and GST, and GST-Syn96–140, a fusion protein of the acidic tail region and GST, were synthesized, respectively (FIG. 1B).

GST-α-synuclein fusion constructs were prepared by PCR amplification of the α-synuclein gene with the specific primers described below and ligating the amplified DNAs after GST gene in the pGEX expression vector (Amersham Pharmacia Biotech). The protein coding regions of the full-length α-synuclein (residues 1–140) was amplified by PCR with the primer 1 (SEQ ID NO:11) containing the underlined BglII restriction site and the primer 2 (SEQ ID NO:12) containing the underlined SalI restriction site and the amino-terminal amphipathic part (residues 1–60) was amplified by PCR with the primer 1 (SEQ ID NO:11) and the primer 3 (SEQ ID NO:13) containing the underlined SalII restriction site. The protein coding regions of the NAC (residues 61–95) was amplified by PCR with the primer 4 (SEQ ID NO:14) containing the underlined BglII restriction site and the primer 5 (SEQ ID NO:15) containing the underlined SalI restriction site and the NAC plus acidic tail (residues 61–140) was amplified by PCR with the primer 4 (SEQ ID NO:14) and the primer 2 (SEQ ID NO:12). The protein coding region of the C-terminal acidic tail (residues 96–140) was amplified by PCR with the primer 6 (SEQ ID NO:16) containing the underlined KpnI restriction site and the primer 7 (SEQ ID NO:17) containing the underlined SalI restriction site. Sequences of the used primers are shown in Table 1.

Table 1

| Primer | DNA Sequence | SEQ ID NO |
|---|---|---|
| 1 Sense | 5'-GCGCTCGAGCCAGATCTGCCATGGATGTATTCATGA-3' | 11 |
| 2 Antisense | 5'-GCGCAAGCTTGTCGACTTAGGCTTCAGGTTCGTAGT-3' | 12 |
| 3 Antisense | 5'-GCGCAAGCTTGTCGACCTATTTGGTCTTCTCAGCCAC-3' | 13 |
| 4 Sense | 5'-GCGCAGATCTCATATGGAGCAAGTGACA-3' | 14 |
| 5 Antisense | 5'-GCGCAAGCTTGTCGACCTAGACTTAGCCAGTGGC-3' | 15 |
| 6 Sense | 5'-GCGCGGTACCGAGATCTGGATGAAAAAGGACCAGTTGGGC-3' | 16 |
| 7 Antisense | 5'-GCGCAAGCTTGTCGACTTAGGCTTCAGGTTCGTAGT-3' | 17 |

The amplified DNAs were purified by electrophoresis using 1% agarose gel, digested with restriction enzymes, then ligated into the restriction enzyme sites of the pGEX vector (Pharmacia Biotech, Buckinghamshire, UK) to construct the expression vectors. All constructs were verified for their sequences by DNA sequencing.

Example 2

Bacterial Expression and Purification of GST-synuclein Fusion Proteins

The expression vectors constructed in Example 1 for expression of GST-synuclein fusion proteins were transformed into the E. coli strain, BL21 (DE3) plysS (Invitrogen). The transformed bacteria were grown in a LB medium containing 0.1 mg/ml ampicillin at 37° C. to an $A_{600}$ of 0.8, induced with 0.5 mM IPTG and then, cultured for a further 4 hours. The culture was then centrifuged at 10,000 rpm for 10 minutes to harvest cells. The cells were resuspended in phosphate-buffered saline (PBS, pH 7.4) and disrupted by ultrasonication. After removing the cell debris, the supernatants were purified by affinity chromatography. That is, the supernatants were passed through a glutathione-Sepharose 4B column (Peptron, Taejeon, Korea) equilibrated with PBS. After washing with PBS, the fusion proteins were eluted with 10 mM GSH (Sigma, St. Louis, Mo). The eluted GST-synuclein fusion proteins were further purified on an FPLC gel-filtration column and concentrated by using CENTRICON filter (Amicon, Beverly, Mass.).

Example 3

Thermal Behavior of α-synuclein and GST Protein

α-synuclein is an "intrinsically unstructured protein" which almost lacks a regular secondary structure and contains a very high portion of random-coil (Plaxco K. W. and Groβ M., Nature, 386, 657–658 (1997); Wright P. E. and Dyson H., J., J. Mol. Biol., 293, 321–331 (1999); Kim J., Molecules and Cells, 7, 78–83 (1997); and Weinreb P. H. et al., Biochemistry, 35, 13709–13715 (1996)). Previous studies have shown that intrinsically unstructured proteins, such as α-synuclein and $α_s$-casein, are heat-resistant since the proteins have a similar unfolded conformation regardless of the temperature and their unfolded conformation is stable at high temperatures as well as at room temperature (Kim T. D. et al., Biochemistry, 39, 14839–14846. (2000)). Therefore, the thermal behavior of α-synuclein and GST protein was initially compared using a qualitative heat-induced protein aggregation assay. The GST and α-synuclein proteins used in this Example were prepared by transforming pGEX vector and pRK172 expression vector containing GST and α-synuclein genes, respectively, into E. coli (Jakes et al., FEBS Letters 345, 27–32 (1994)). The recombinant GST protein was purified by the same method as described in Example 2 and the recombinant α-synuclein was purified according to the known method (Kim J., Molecules and Cells, 7, 78–83 (1997); Paik S. R. et al., Arch. Biochem. Biophys., 344, 325–334 (1997)).

The heat-induced aggregation of GST and α-synuclein protein was qualitatively assayed by SDS polyacrylamide gel after heat treatment of the samples. Each protein suspended in PBS (0.6 mg/ml) was heated in a boiling water bath for 10 minutes and cooled in the air. The protein samples were centrifuged at 15,000 rpm for 10 minutes and the supernatants were analyzed on a 12% SDS polyacrylamide gel. The protein bands were stained with Coomassie Brilliant blue R250.

Figure 2:
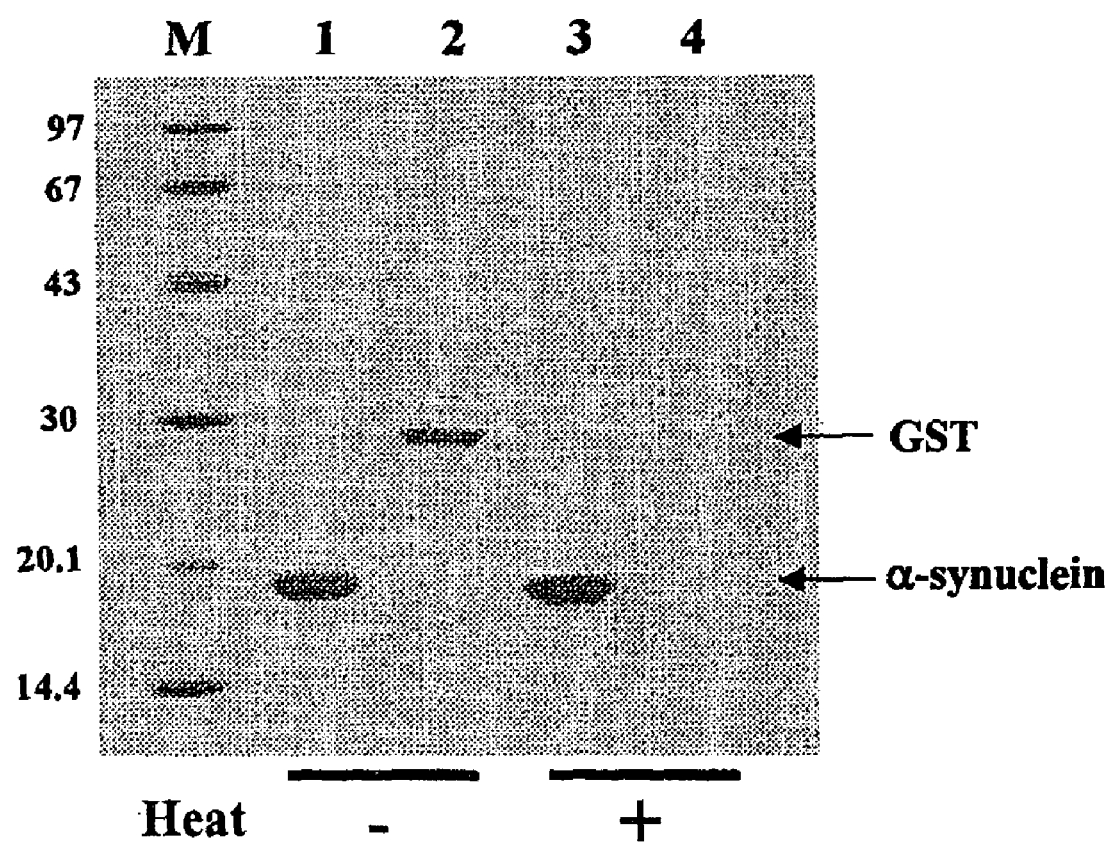
FIG. 2 is the results of SDS-polyacrylamide gel eletrophoresis (SDS-PAGE) showing thermal behaviors of α-synuclein and the GST protein (Lane 1: α-synuclein without heat treatment, Lane 2: GST without heat treatment, Lane 3: α-synuclein with heat treatment, Lane 4: GST with heat treatment)

As expected, α-synuclein did not precipitate upon heat treatment, whereas the GST protein did (FIG. 2). For α-synuclein, the protein bands were observed when both heat-treated and non-heat-treated. However, for GST protein, the protein bands were observed when non-heat-treated but were not observed after heat-treated. Thus, it was noted that α-synuclein is a heat-resistant protein while GST is a heat-labile protein. Such experimental results were reproducible regardless of the pH and salt concentration of the buffer solution and the protein concentration (data now shown).

Example 4

Thermal Behavior of α-synuclein Deletion Mutants

Next, a series of deletion mutants were used to determine the domain, inducing heat resistance of α-synuclein. The GST-synuclein fusion proteins prepared in Example 2 were treated with 1 unit of thrombin per 1 mg of protein for 2 hours at room temperature to cleave the α-synuclein fragments from the GST fusion proteins. The resulting α-synuclein deletion mutants were examined for their thermal stability.

According to the same method with Example 3, the cleaved products obtained by thrombin digestion were examined for their thermal stability. The obtained α-synuclein deletion mutants include two deletion mutants (Syn61–140, Syn96–140), each containing the ATSα (residues 96–140), a deletion mutant containing α-synuclein N-terminal (Syn1–60) and a deletion mutant containing the hydrophobic NAC region (Syn61–95).

Figure 3:
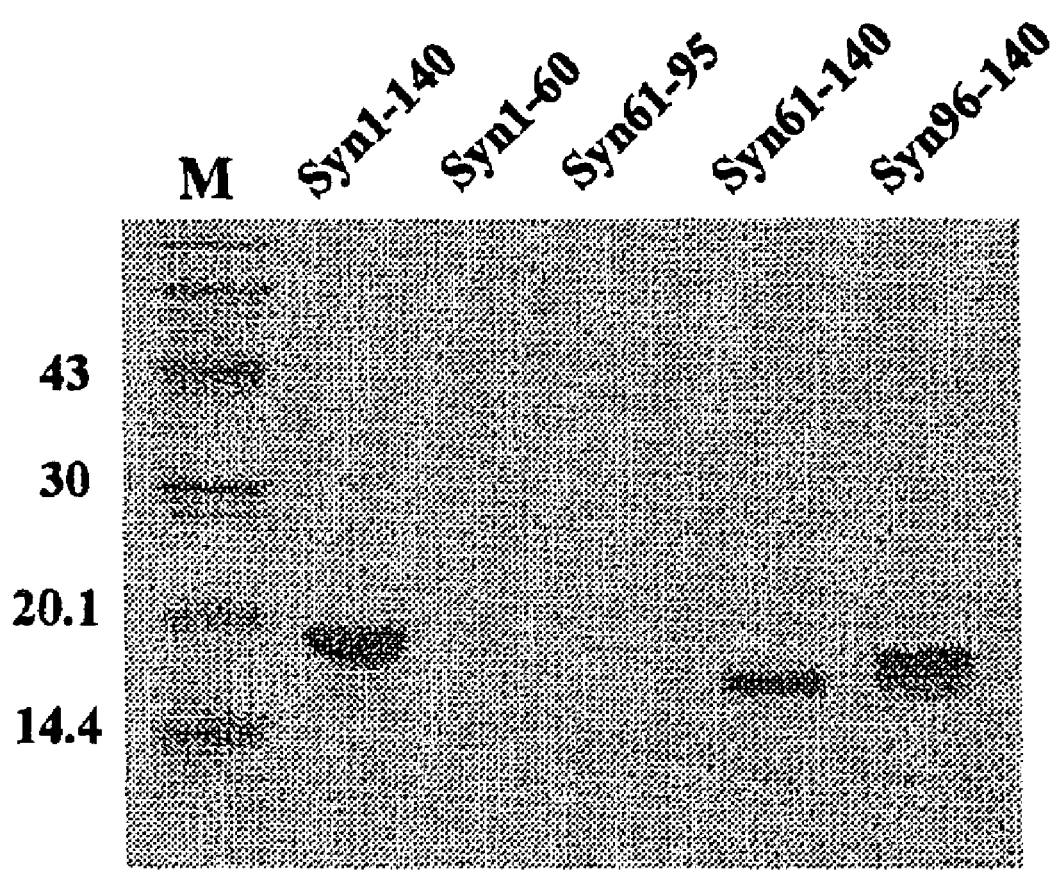
FIG. 3 is the results of SDS-PAGE showing thermal behaviors of α-synuclein deletion mutants, prepared by treating the GST-α-synuclein fusion proteins with thrombin.

Wild type (Syn1–140) and two deletion mutants containing the ATSα (Syn61–140, Syn96140) did not precipitate and hence, protein bands were observed in an analysis using an SDS polyacrylamide gel after heat treatment. This indicated that the two proteins are heat-resistant. In contrast, the N-terminal part of α-synuclein (Syn1–60) and the NAC peptide (Syn61–95) appeared to precipitate upon heat treatment and hence, no protein band was observed (FIG. 3). From these results, only the deletion mutants containing the ATSα were found to be heat-resistant. Accordingly, it was noted that the ATSα is responsible for the heat resistance. Consistent with data of the inventors, previous studies have shown that C-terminally truncated α-synuclein proteins and the NAC peptide assembled into filaments much more readily than the wild type protein (Serpell L. C. et al., Proc. Natl. Acad. Sci. USA, 97, 4897–4902 (2000); Crowther R. A. et al., FEBS Letters, 436, 309–312 (1998); Han H. et al., Chem. Biol., 2, 163–169 (1995); and Iwai A. et al., Biochemistry, 34, 10139–10145 (1995)). Overall, it appears likely that C-terminally truncated α-synuclein mutant proteins are less stable at room temperature and higher temperature than both the wild type and mutant proteins containing the C-terminal acidic tail. Thus, it is noted that the ATSα plays a very important role for thermosolubility of α-synuclein.

Example 5

Thermal Behavior of GST-synuclein Fusion Proteins

The thermal behaviors of GST-synuclein fusion proteins, prepared as in Example 2, were investigated. Using the same method as described in Example 3, the GST-α-synuclein fusion proteins were boiled in a boiling water bath for 10 minutes. The protein solutions were centrifuged and the supernatants were analyzed on a SDS polyacrylamide gel. Also, the thermal behaviors of GST-α-synuclein fusion proteins were quantitatively by monitoring absorbance at 360 nm according to time (Lee G. J. and Vierling E., Method Enzymol., 290, 360–65 (1998); Horwitz J. Proc. Natl. Acad. Sci. USA 89, 10449–53 (1992)).

Figure 4A:
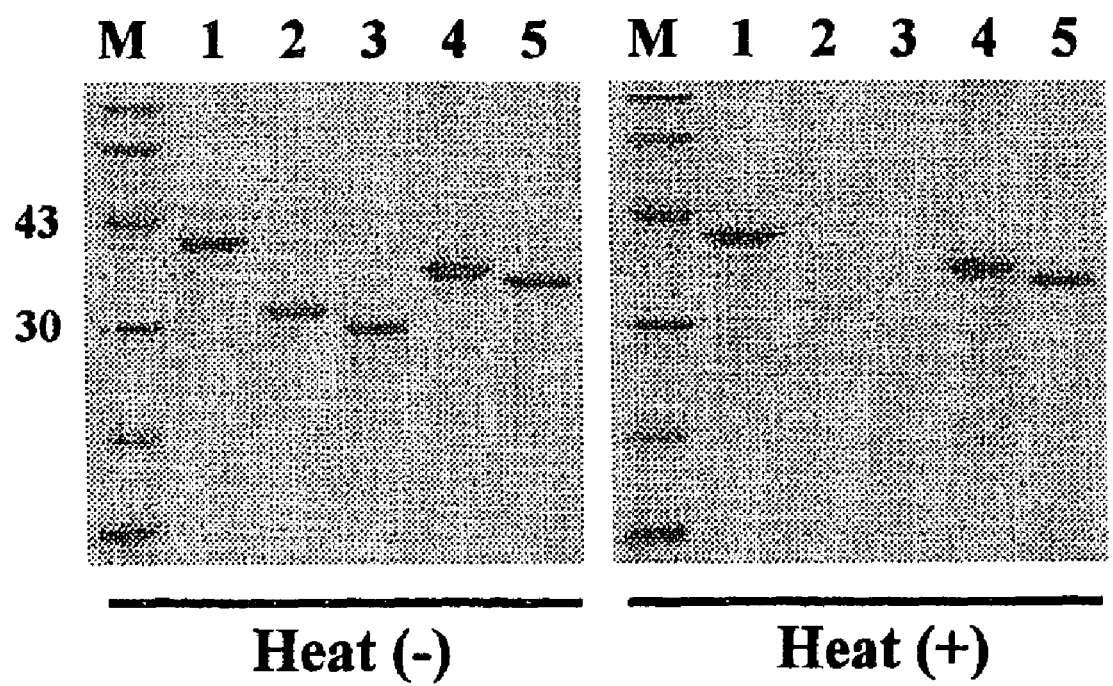
FIG. 4A is the results of SDS-PAGE showing thermal behaviors of GST-α-synuclein fusion proteins before (left panel) and after (right panel) boiling (Lane 1: GST-Syn-140, Lane 2: GST-Syn1–60, Lane 3: GST-Syn61–95, Lane 4: GST-Syn61–140, Lane 5: GST-Syn96–140)

In the experiment, as shown in FIG. 4A, GST-Syn1–140, GST-Syn61–140 and GST-Syn96–140 shows protein bands both before and after heat treatment, indicating that these proteins did not precipitate upon heat treatment. Therefore, it is noted that they are heat-resistant. Whereas, for GST-Syn1–60 and GST-Syn61–95, protein bands were observed before heat treatment, but not observed after heat treatment. Therefore, it is noted that these proteins are heat-labile and had completely precipitated upon heat treatment.

Figure 4B:
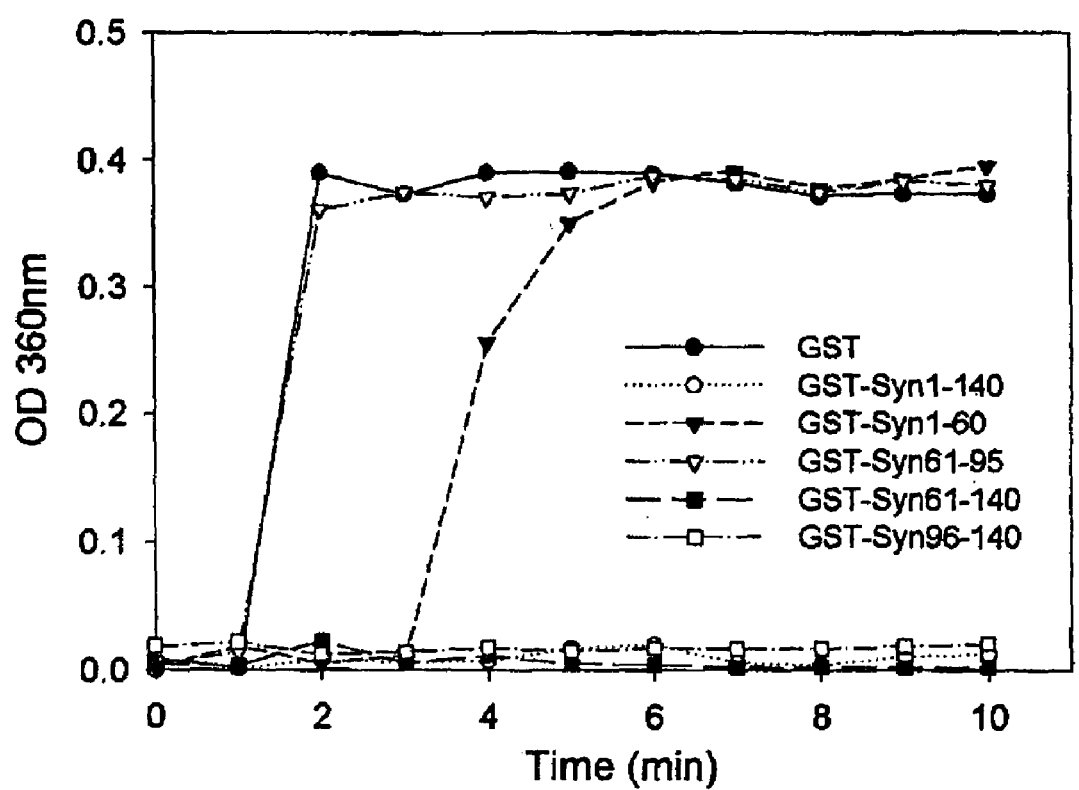
FIG. 4B is a graph of absorbance showing heat-induced aggregation of the GST-α-synuclein fusion proteins.

Also, the heat-induced aggregation of the GST-synuclein fusion proteins was quantitatively analyzed by measuring the turbidity at 65° C. according to time. As shown in FIG. 4B, the $OD_{360}$ of the GST protein drastically increased 2 minutes after heat treatment, and most of the protein had aggregated by 3 minutes. GST-Syn61–95 behaved similarly to the GST protein, and resulted in complete aggregation. GST-Syn1–60 also resulted in complete aggregation after heat treatment, although aggregation of this protein was relatively delayed. Consistent with the results in FIG. 4A, there was no evidence of any protein aggregation for GST-Syn1–140, GST-Syn61–140 and GST-Syn96–140 even after heat treatment of 30 minutes. Interestingly, these three heat-resistant GST-synuclein fusion proteins all contain the ATSα. From these results, it is noted that a heat-labile protein can be transformed into a heat-resistant protein by introducing the ATSα.

Example 6

PI and Hydropathy Values of α-synuclein Deletion Mutants, GST and GST-Synuclein Fusion Proteins Previously, many of the heat-resistant proteins from Jurkat T cell lysates and human serum were reported to be highly acidic proteins. This implies that the pI value may be related to heat-resistance of proteins (Kim T. D., et al., Molecules and Cells, 7, 78–83 (2000)). The solubility of proteins may play an important role in determining the heat-resistance, since highly charged proteins would be soluble even at higher temperatures. To confirm this hypothesis, the pI and hydropathy values of α-synuclein deletion mutants were compared with those of GST and GST-synuclein fusion proteins (Table 2). The pI and hydropathy values were calculated using ProtParam program.

From the results, as shown in Table 2, heat-resistant proteins, such as α-synuclein, Syn61–140, Syn96–140, GST-Syn1–140, GST-Syn61–140 and GST-Syn96–140, have abnormally low pI and hydropathy values. On the other hand, the heat-labile proteins with the exception of Syn61–95 show much higher values. Interestingly, Syn61–95, a heat-labile peptide shows a very low pI value but it has an extremely high hydropathy value. Therefore, it is possible that highly charged proteins with a low hydropathy value possesses an advantage in resisting heat-induced protein aggregation.

TABLE 2

| Protein | Temperature Reaction | Pi Value[a] | Hydropathy[b] |
|---|---|---|---|
| α-Synuclein | HR[c] | 4.67 | −0.403 |
| Syn1–60 | HL[d] | 9.52 | −0.188 |
| Syn61–95 | HL | 4.53 | 0.726 |
| Syn61–140 | HR | 3.85 | −0.564 |
| Syn96–140 | HR | 3.76 | −1.567 |
| GST | HL | 6.18 | −0.390 |
| GST-Syn1–140 | HR | 5.25 | −0.378 |
| GST-Syn1–60 | HL | 7.64 | −0.349 |
| GST-Syn61–95 | HL | 6.01 | −0.244 |
| GST-Syn61–140 | HR | 4.95 | −0.435 |
| GST-Syn96–140 | HR | 4.85 | −0.560 |

[a]pI value was calculated by using ProtParam program.
[b]Hydropathy value was calculated by using ProtParam program.
[c]HR, heat-resistant
[d]HL, heat-labile Example 7

Effect of Divalent Cation Binding

Several divalent cations, such as $Cu^{2+}$ and $Ca^{2+}$, are known to bind specifically to the ATSα region with a dissociation constant in the micromolar range (Paik S. R. et al., Biochem. J., 340, 821–8 (1999); and Nielsen M. S. et al., J. Biol. Chem., 276, 22680–22684). $Zn^{2+}$ also is known to bind specifically to α-synuclein, although the binding sites are not yet identified (Paik S. R. et al., Biochem. J., 340, 821–8 (1999); and Kim T. D. et al., Biochemistry, 39, 14839–14846 (2000)). Since the ATSα is important for heat-resistance of proteins, the effect of the divalent cation binding on the heat-induced aggregation of GST-synuclein fusion proteins containing the ATSα was investigated. As divalent cations, $CaCl_2$, $MgCl_2$ and $ZnCl_2$ were used. The GST-Syn1–140, GST-Syn61–140 and GST-Syp96–140 fusion proteins were diluted to a final concentration of 0.2 mg/ml in 20 mM Tris-HCl buffers containing 0 to 1.0 mM of respective divalent cations. The protein solutions were reacted at 65° C. for 30 minutes and their apparent absorbances were measured at 360 nm.

Figure 5A:
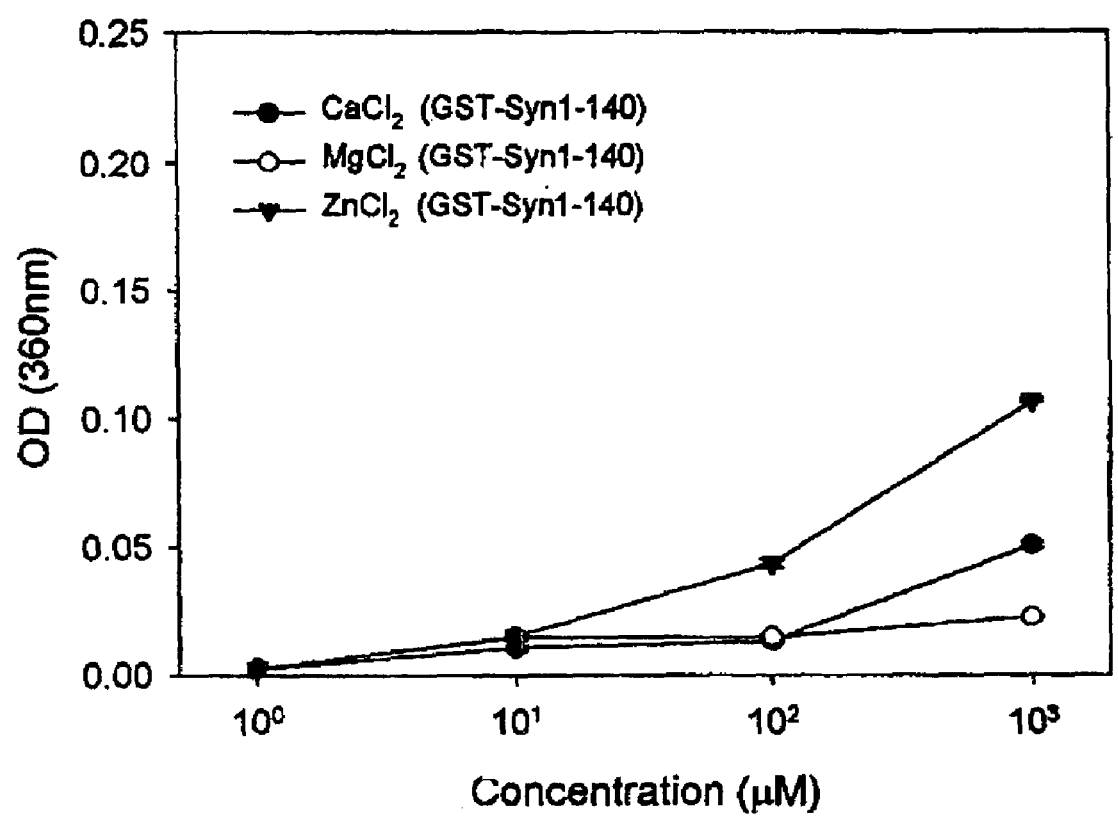
FIG. 5A is a graph of absorbance showing effect of divalent cations on the heat-induced aggregation of GST-Syn1–140.
Figure 5B:
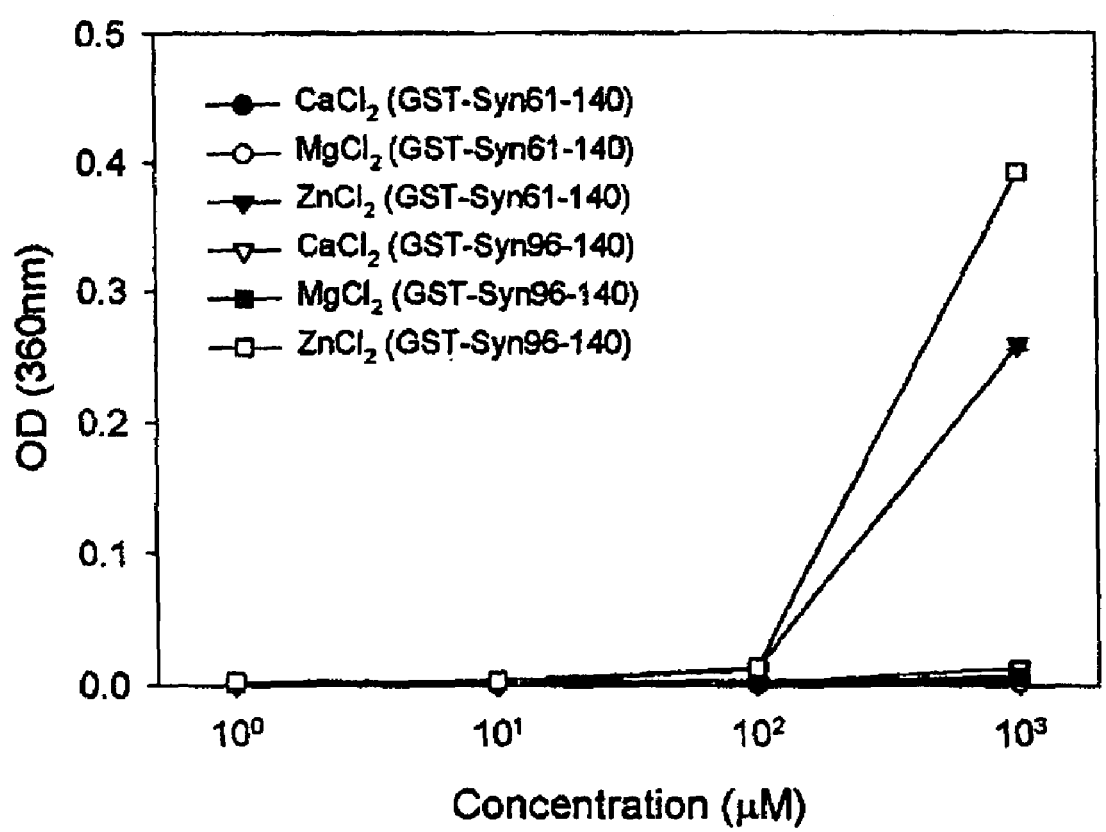
FIG. 5B is a graph of absorbance showing effect of divalent cations on the heat-induced aggregation of GST-Syn61–140 and GST-Syn96–140.

From the results as shown in FIG. 5A and FIG. 5B, it was found that low concentrations of the divalent cations do not affect the heat-induced aggregation of the fusion proteins. However, high concentrations significantly increased the protein aggregation, although the fusion proteins did not completely precipitate. Particularly, $Zn^{2+}$ appeared to be most effective for enhancing the heat-induced protein aggregation. The dissociation constants between α-synuclein and the divalent cations were considerably low, and most proteins were affected by a high concentration of metal ions. Therefore, the results suggest that the specific binding of the divalent cations at the ATSα region does not affect the thermal behavior of the fusion proteins. However, it was noted that nonspecific binding of the metal ions at a high concentration induces more protein aggregation during heat treatment.

Example 8

GST Activity of GST-synuclein Fusion Proteins After Heat Treatment

Unlike the wild type GST protein described in the foregoing Examples, GST-synuclein fusion proteins containing the ATSα were found to be heat resistant. This suggests that the heat-labile protein could be transformed into a heat-resistant protein simply by introducing the ATSα. Subsequently, whether or not the heat-resistant GST-fusion proteins could keep the enzymatic activity after heat treatment was investigated. The GST and GST-synuclein fusion proteins were boiled in a water bath for 10 minutes and cooled in the air at room temperature. The enzymatic activities of these heat-treated proteins were then compared. The enzymatic activity was assayed using a chromogenic substrate, 1-chloro-2,4-dinitro benzen (DTNB) (Habig W. H. et al., J. Biol. Chem., 249, 7130–7139 (1974)). The purified GST and GST-synuclein fusion proteins were diluted into the substrate solution (1 mM GSH and 2 mM DTNB dissolbed in 0.1 M phosphate buffer, pH 7.4) to a final concentration of 20 μg/ml and incubated at 37° C. for 10 minutes. Upon completion of incubation, the enzymatic activity was assayed by measuring absorbance at 350 nm. The absorbance was measured on a SPECTRAMAX 250 microplate reader (Molecular Devices, CA, USA).

Figure 6A:
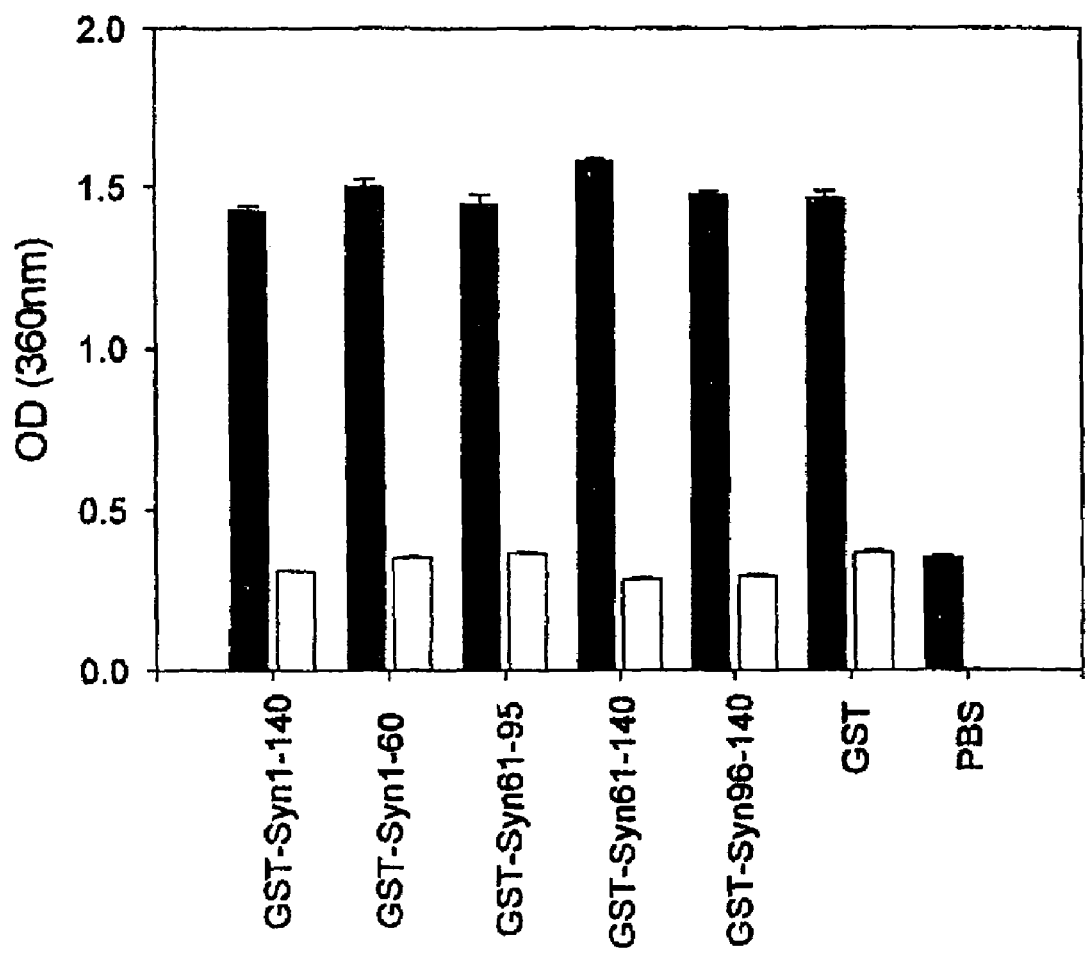
FIG. 6A is a graph of absorbance for comparison of GST activities of GST and the GST-synuclein fusion proteins before and after heat treatment (□: before heat treatment, ▫: after heat treatment)
Figure 6B:
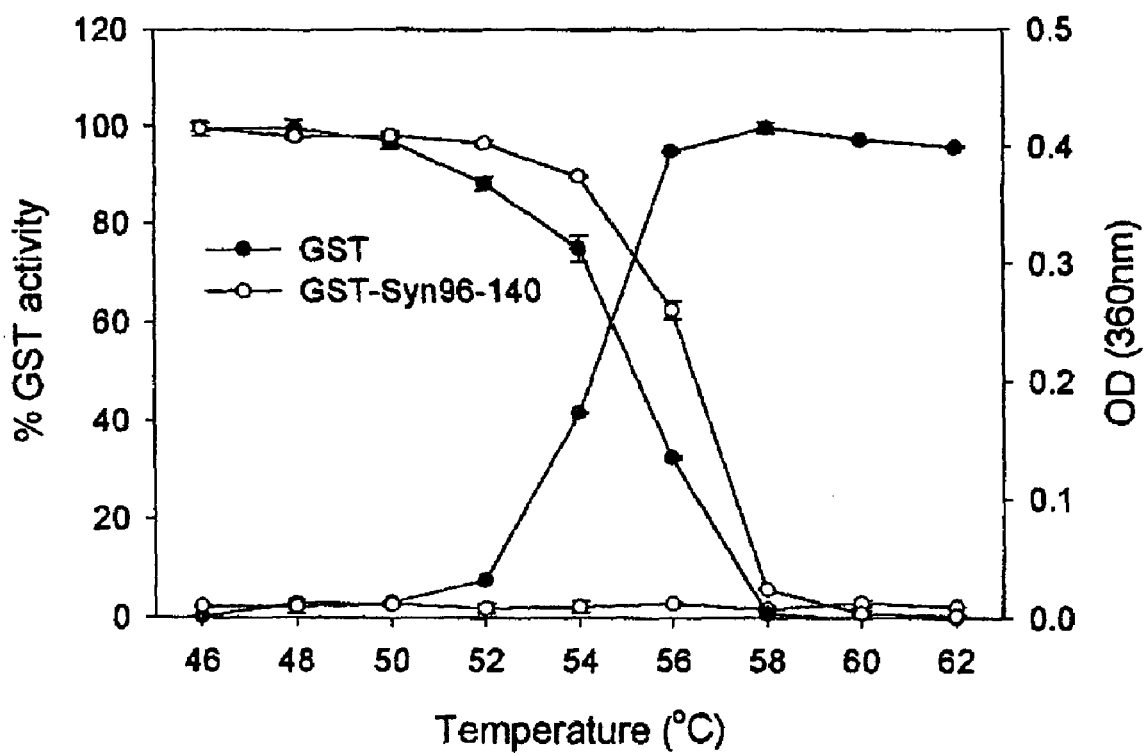
FIG. 6B is a graph of absorbance for showing enzyme activity (Left) and aggregation profile (Right) of GST and the GST-Syn96–140 according to temperature (-○-: GST, -●-: GST-Syn96–140, bars indicating the standard deviation)

From the results, as shown in FIG. 6A, all the GST and GST-fusion proteins completely lost their enzymatic activity under these stringent conditions. Subsequently, the thermostabilities of GST and GST-Syn96–140 were quantitatively measured by thermal inactivation curves (FIG. 6B), which were used to determine the $T_{50}$ values, the temperatures at which 50% of initial enzymatic activity was lost after heat treatment. As shown in FIG. 6B, the $T_{50}$ of GST-Syn96–140 is about 2° C. higher than that of GST. Interestingly, the thermal inactivation of GST is well correlated with the thermal aggregation of the protein. It is noted that the introduced ATSα is able to protect the enzyme from the thermal inactivation by preventing the thermal aggregation of the fusion protein.

Example 9

Heat-induced Structural Changes of GST-Syn96–140

Previously, heat-induced secondary structural changes of α-synuclein assayed by CD analysis has been reported (Kim T. D. et al., Biochemistry, 39, 14839–14846 (2000)). The CD spectrum of α-synuclein indicated that the protein almost completely lacks secondary structural elements. Also, it was shown that the CD spectrum of α-synuclein at 100° C. was slightly different from that at 25° C. but it represented the characteristics of random-coiled polypeptides. Consistent with these results, a linear temperature-dependence of the CD signal, often seen with unfolded peptides, was observed.

The present inventors analyzed the secondary structural changes of GST due to thermal denaturation by measuring CD spectra of GST and the GST-Synclein fusion protein. The CD spectra were recorded on a JASCO-J715 spectropolarimeter (Jasco International Co. Ltd., Tokyo, Japan) equipped with a temperature control system in a continuous mode. The far-UV CD measurements were carried out over the wavelength range of 190 to 250 nm with 0.5 nm bandwidth, a one second response time and a 10 nm/minute scan speed at 25 0C and 100 0C. The spectra shown are an average of five scans that were corrected by subtraction of the buffer signal. The CD data were expressed in terms of the mean residue ellipticity, $(deg.cm^2.dmol^{-1})$. The protein samples for CD measurements were prepared in 10 mM sodium phosphate buffer, unless otherwise specified, and all spectra were measured in a cuvette with a path length of 0.1 cm.

Thermal denaturation experiments were performed using a heating rate of 1° C./min and a response time of 1 second. The thermal scan data were collected from 25 to 100° C. The concentrations of GST and the GST-Syn96–140 were 0.1 mg/ml and 0.3 mg/ml, respectively. The CD spectra were measured every 0.5° C. at a wavelength of 222 nm, unless otherwise specified. The reversibility of the thermal transition was examined by comparing a new scan recorded by decreasing the temperature and another scan recorded by cooling the thermally unfolded protein sample.

Figure 7A:
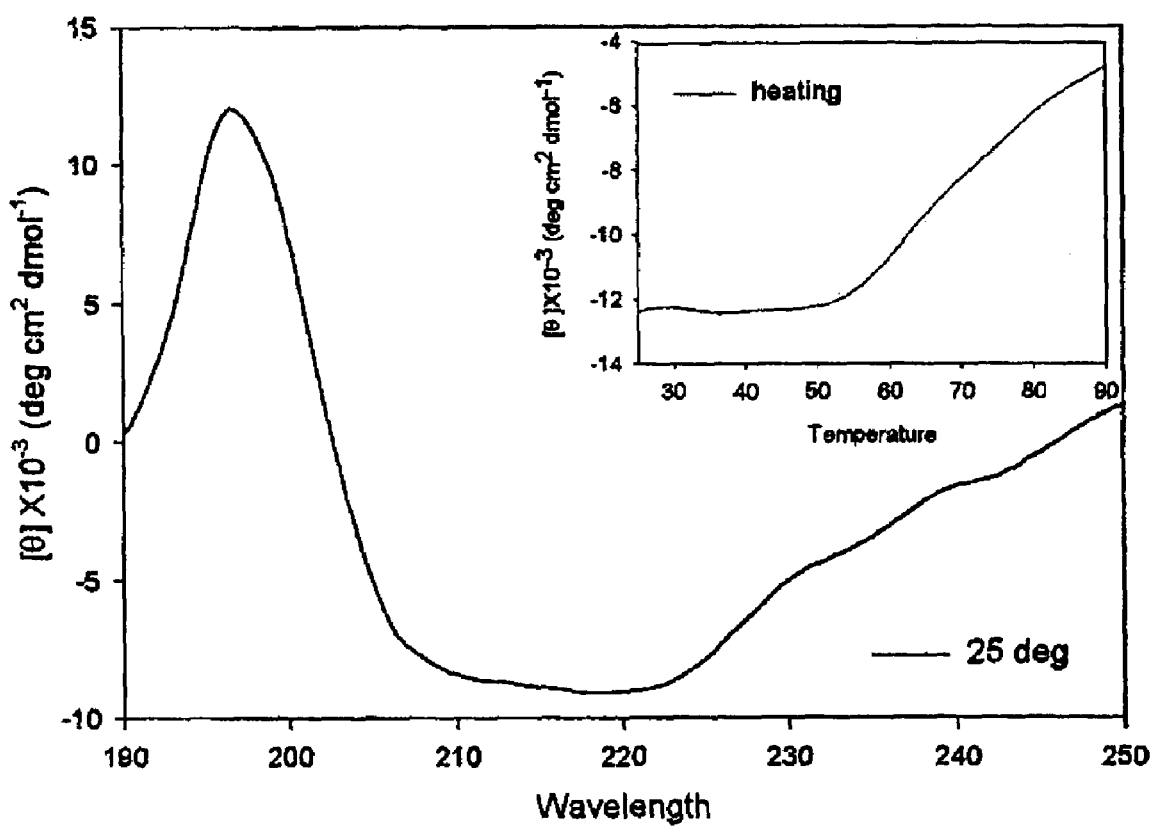
FIG. 7A is a graph showing far-UV CD spectrum and the melting curve of GST (the inserted graph presenting the mean molar ellipticity per residue of the GST protein at 222 nm according to temperature)

From the CD spectrum of GST at 25° C., as shown in FIG. 7A, it was found that the protein contains well ordered secondary structural elements. However, at 100° C., the far-UV CD spectrum almost disappeared due to protein precipitation (data not shown). Through the heat-induced changes in the ellipticity of the GST at 222 nm, the Tm of GST was found to be approximately 70° C. The GST had completely precipitated at 100° C. and a CD signal was not observed at 222 nm, which indicates that GST had irreversibly precipitated (data not shown). These results confirm that the GST protein is a typical heat-labile protein which unfolds and precipitates as the temperature is increased.

Figure 7B:
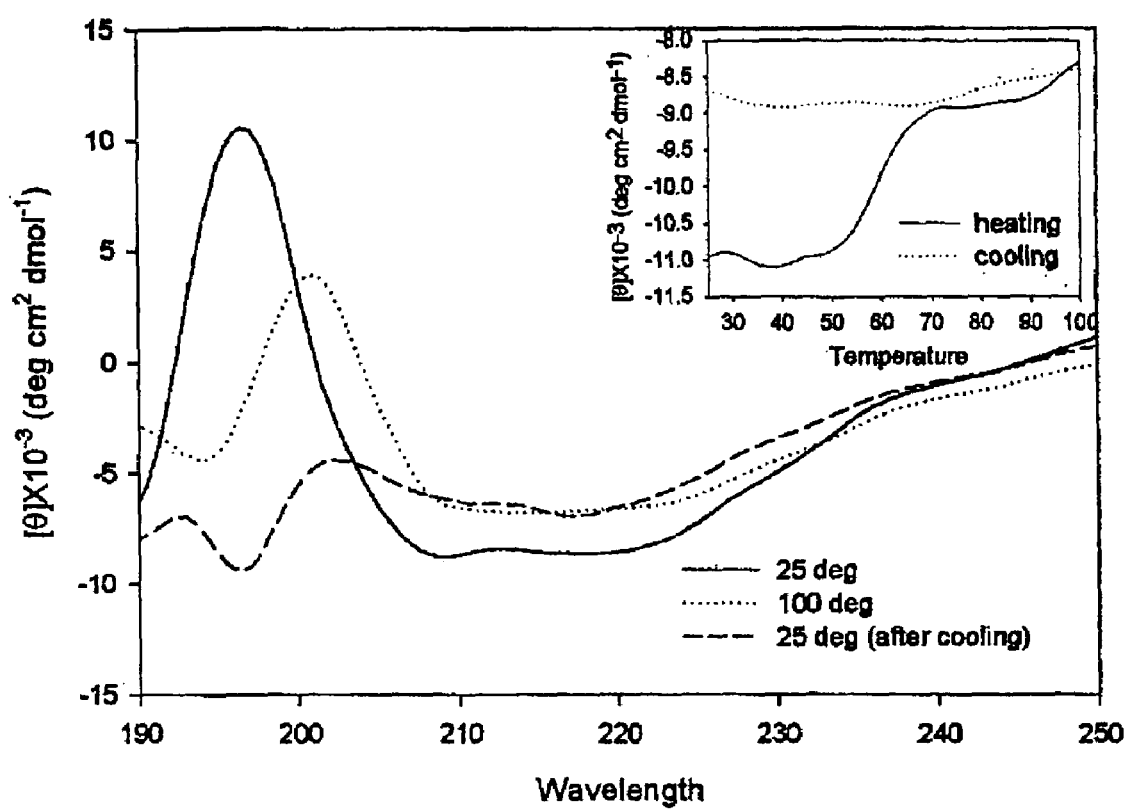
FIG. 7B is a graph showing far-UV CD spectrum and the melting curve (inserted graph) of GST-Syn96–140 (solid line: measurement at 25° C., dotted line: measurement at 100° C., dashed line: measurement after cooling from 100° C. to 25° C.)

The far-UV CD spectra of GST-Syn96–140 are shown in FIG. 7B. The far-UV CD spectrum of GST-Syn96–140 at room temperature (solid line) indicates that the protein contains well-ordered secondary structural elements. The CD spectrum showed a decrease in these elements at 100° C. but the overall shape was unchanged (dotted line). These results mean that heating does not lead to complete unfolding. Interestingly, a new absorption band at 195 nm appears, which is characteristic of random-coiled polypeptides. After cooling the protein solutions, the far-UV CD spectrum is distinguishable from the initial one (dashed line), which indicates that the conformation of GST-Syn96–140 may be irreversibly changed. The CD spectrum of the heat-treated GST-Syn96–140 at room temperature rather resembles that obtained at 100° C., which indicates that the protein consists of two distinct domains: one with regular secondary structural elements and the other with a random-coil like conformation. To confirm the conformational changes induced by heating, the GST-Syn96–140 melting curves were measured according to temperature. The heat-induced changes in the ellipticity at 222 nm are presented in FIG. 7B. Interestingly, the heat-induced unfolding of GST-Syn96–140 appeared to take place in two stages. The first transition was observed at 62° C. and the second transition observed at 95° C. As expected, the temperature curves of GST-Syn96–140 appeared to be irreversible (dotted line).

GST is a heat-labile protein, while GST-Syn96–140 is a heat-resistant protein. To compare the stability of the two proteins, it would be useful to determine the Tm of both proteins. However, it is difficult to directly compare the Tm values of GST-Syn96–140 and GST, since these proteins contain different number of peptide domains. Interestingly, the Tm value of GST-Syn96–140 (62° C. for the first transition) appears to be slightly lower than that of GST (70° C. for the first transition). Since the Tm of a given protein is related to the change in the free energy between the native and thermally denatured state of the protein, the Tm has been used as a thermodynamic parameter of the conformational stability of the protein. Therefore, it is noted that introduction of the ATSα to the C-terminus of GST is favorable for protein stability against environmental stress such as increased temperature and consequently for heat-resistance, but unfavorable for intrinsic thermal stability of the protein.

Example 10 pH- and Metal-induced Protein Aggregation

The pH-induced aggregation of GST and GST-Syn96–140 was investigated by measuring the turbidity at 65° C. according to time. The measurement of the turbidity was carried out by monitoring the apparent absorbance at 360 nm according to time. Each protein was diluted to a final concentration 0.2 mg/ml in buffers with different pH values. The buffers used were 0.1 M acetate (pH 4.0 and 5.0), 0.1 M citrate (pH 6.0), and 0.1 M Tris-HCl (pH 7.4). The protein solutions diluted in buffers were incubated for 1 hour at room temperature and their apparent absorbance were measured in a BECKMAN DU650 spectrophotometer Beckman Coulter, Fullerton, Calif.). The metal-induced aggregation of GST and GST-Syn96–140 was similarly assessed. Each protein was diluted to a final concentration of 0.2 mg/ml in 20 mM Tris-HCl buffers containing 0 to 1.0 mM of $Zn^{2+}$, or $Cu^{2+}$. The protein solutions were incubated for 30 minutes at room temperature and their apparent absorbances at 360 nm were measured.

Figure 8A:
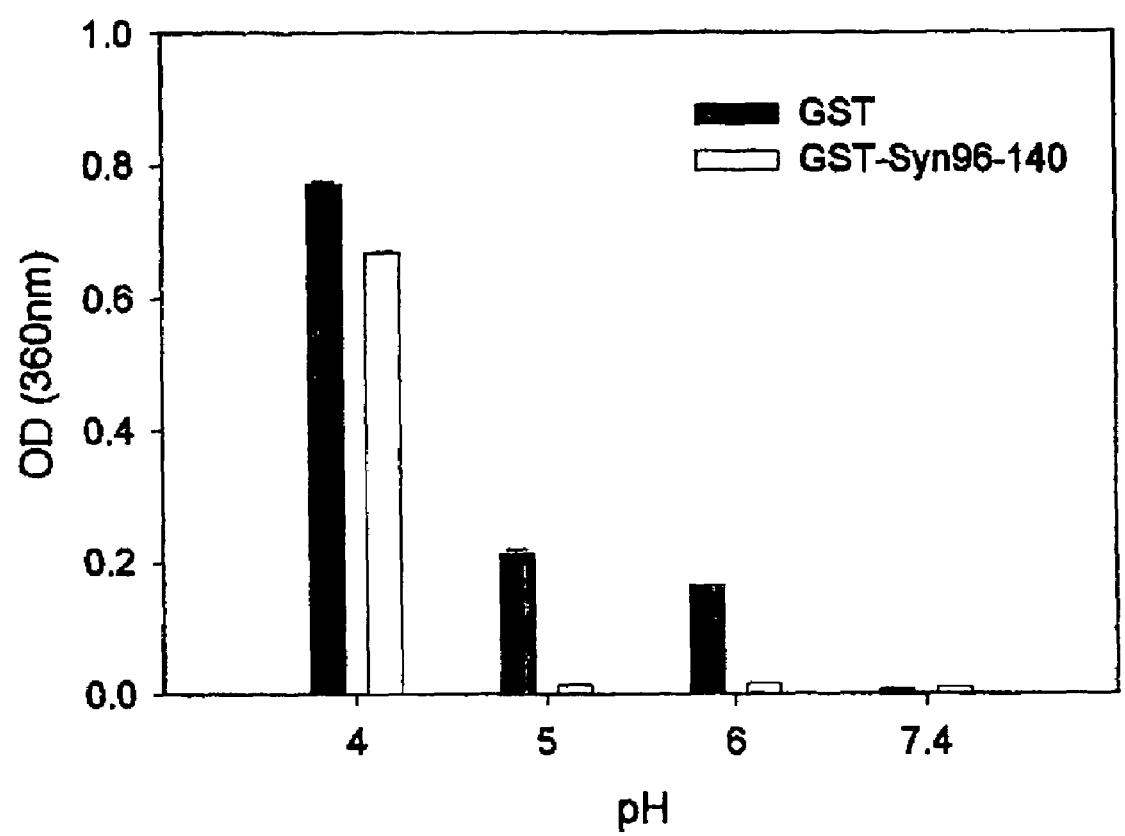
FIG. 8A is a graph showing pH-induced aggregation of GST and GST-Syn96–140.
Figure 8B:
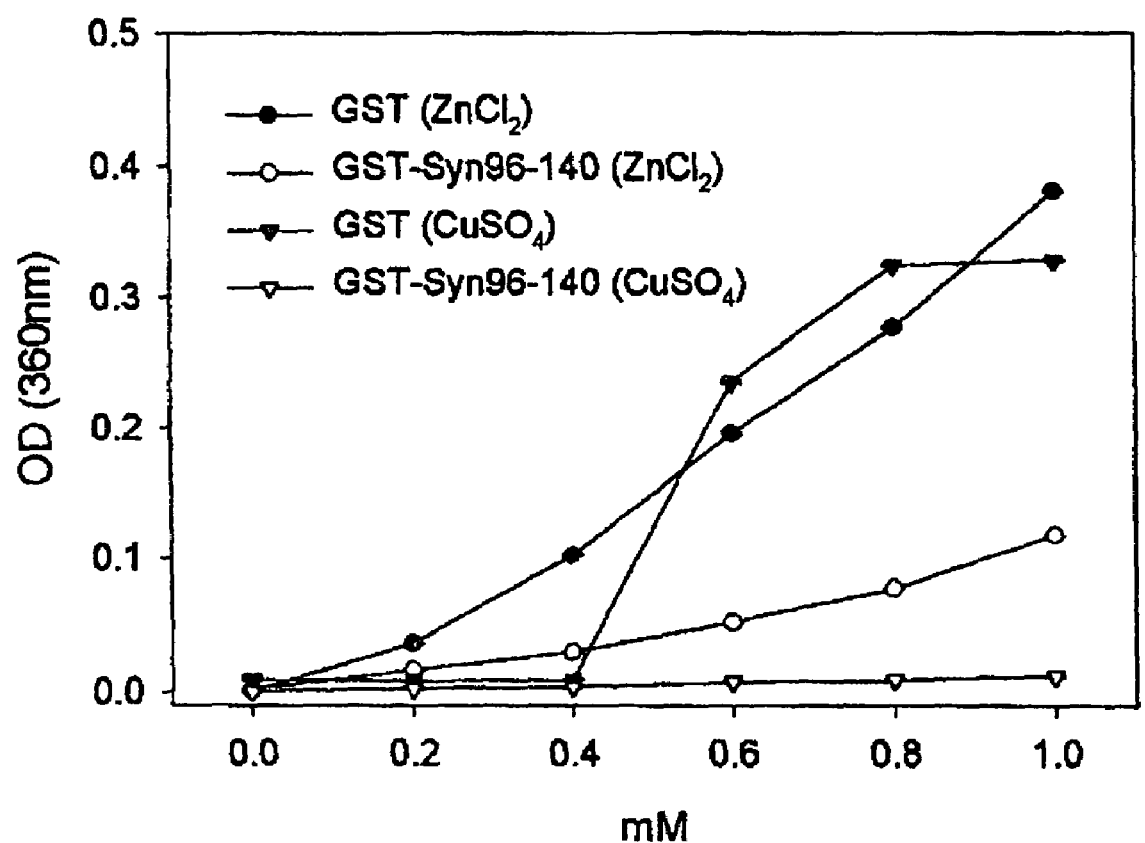
FIG. 8B is a graph showing metal-induced aggregation of GST and GST-Syn96–140.

The results of the pH-induced aggregation of the proteins were shown in FIG. 8A. The $OD_{360}$ of the GST protein steadily increased from pH 7.4 to pH 5.0 and reached maximum value at pH 4.0. On the other hand, the $OD_{360}$ of GST-Syn96–140 was not changed until pH 5.0, but drastically increased at pH 4.0, perhaps due to the neutralization of the acidic tail. From these results, it is noted that the ATSα does not show sufficient protective effect under very acidic conditions but can completely protect GST from aggregation induced by pH 4.5 or higher. The results of the metal-induced aggregation of the proteins are shown in FIG. 8B. The ATSα also appeared to protect GST from metal-induced aggregation. The $OD_{360}$ of the GST protein steadily increased when it was treated with 0.2 to 1.0 mM $Zn^{2+}$, while the $OD_{360}$ of GST-Syn96–140 was always much lower than that of GST. In particular, $Cu^{2+}$-induced protein aggregation was completely blocked by introducing ATSα. From these results, it is noted that the ATSα can also protect GST from metal-induced aggregation.

Example 11

Effect of the ATSα on Stress-induced Aggregation of DHFR

In order to examine whether any fusion proteins with the ATSα other than GST-ATSα show resistance to environmental stresses, the present inventors constructed a DHFR-synuclein fusion protein, DHFR-ATSα, which contains the ATSα at the C-terminus.

The protein coding region of DHFR was subcloned into an *E. coli* expression vector, pRSETA, using BamHI and HindIII restriction sites (pDHFR). The protein coding region of the ATSα (residues 96–140) was amplified by PCR with 5'-oligonucleotide primer (Table 3, SEQ ID NO:18) containing the underlined KpnI restriction site and 3-oligonucleotide primer (SEQ ID NO:19) containing the underlined SalI restriction site. The amplified DNAs were gel purified, digested with appropriate enzymes, ligated into the pDHFR vector which had been digested with appropriate restriction enzymes, and gel purified. The resulting expression vector (pDHFR-ATSα) was verified by DNA sequencing.

TABLE 3

| Primer | | Sequence |
|---|---|---|
| 8 | Sense | GCGCGGTACCAAGGACCAGTTGGGCAAGAATG (SEQ ID NO:18) |
| 9 | Antisense | GCGCGTCGACTTAGGCTTCAGGTTCGTAGT (SEQ ID NO:19) |

The expression vector (pDHFR-ASTα) was transformed into the *E. coli* strain, BL21 (DE3), for protein expression. The transformed bacteria were grown in a LB medium containing 0.1 mg/mi ampicillin at 37° C. to an $A_{600}$ of 0.8. 0.5 mM 1PTG was added to the medium, which was cultured for a further 4 hours. The culture was centrifuged at 10,000 rpm for 10 minutes to harvest cells. The cells were resuspended in phosphate-buffered saline (PBS, pH 7.4), and disrupted by ultrasonication. After removing the lysed strains, the supernatants were loaded onto a Ni-NTA column equilibrated with a loading buffer (50 mM phosphate buffer (pH 8.0) containing 0.3M NaCl and 10 mM imidazole). After washing with the loading buffer, the protein was eluted with 250 mM imidazole in the same buffer, the DHFR-ATSα was further purified on an FPLC gel-filtration column. The purified protein was concentrated and buffer-changed by CENTRICON filter (Amicon, Beverly, Mass).

The heat resistance of the DHFR-ATSα fusion protein was compared with that of DHFR. Each protein suspended in PBS (0.2 mg/ml) was heated in boiling water baths at 65° C. and 100° C. for 10 minutes each and cooled in air. The protein samples were centrifuged at 15,000 rpm for 10 minutes and the supernatants were analyzed on a 12% SDS polyacrylamide gel. The protein bands on the SDS polyacrylamide gel were stained with Coomassie Brilliant blue R250 to be visible.

Figure 9:
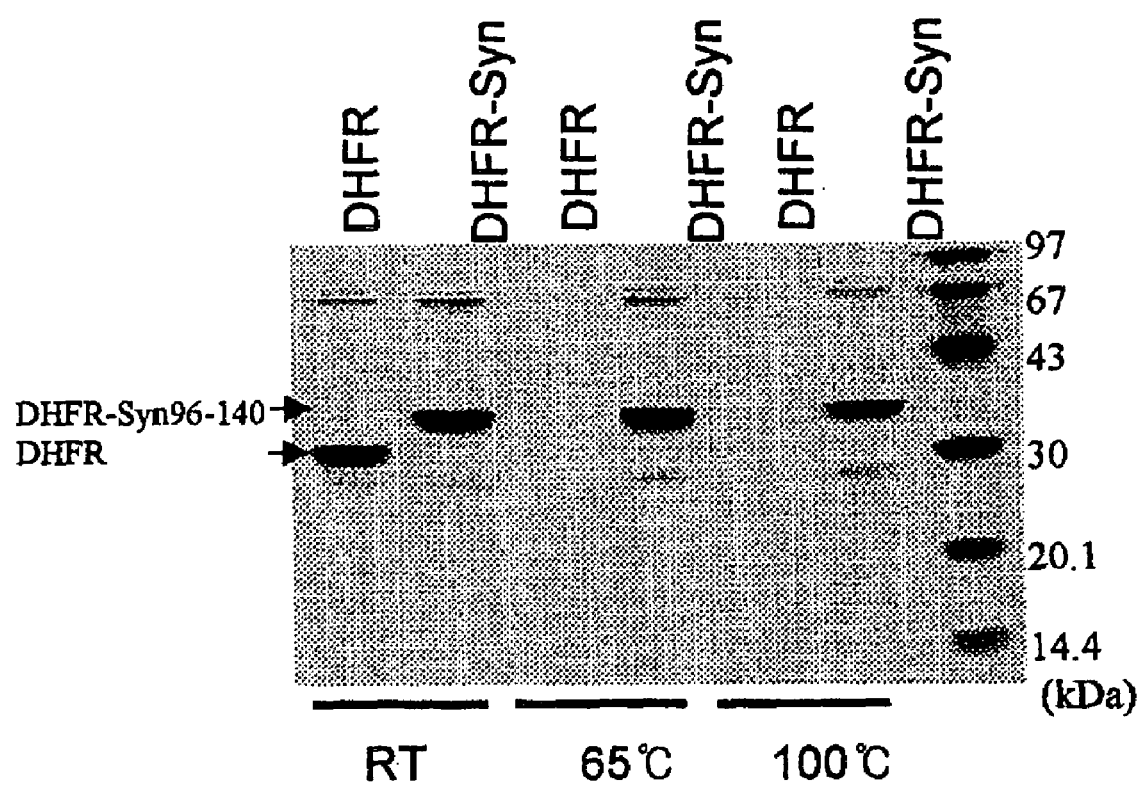
FIG. 9 is the results of SDS-PAGE showing thermal behavior of the DHFR-Syn96–140 fusion protein before heat treatment and after heat treatment at 65° C. and 100° C., respectively, for 10 minutes (the last lane is a size marker protein)

As shown in FIG. 9, for DHFR-ATSα, the protein bands were observed both before heat treatment and after heat treatment at 65° C. and 100° C., which indicates that no precipitation due to heat treatment takes place. On the other hand, DHFR, the protein bands were observed before heat treatment but not after heat treatment. This indicates that the protein was completely precipitated by heat treatment and is heat-labile. Thus, it was noted that wild type DHFR is a heat-labile protein, which readily precipitates by thermal stress while DHFR-ATSα according to the present invention has a high heat-resistance. That is, it is demonstrated that ATSα is a peptide capable of providing heat resistance to DHFR and other proteins, as well as GST.

Example 12

Heat-resistance of GST-synuclein Fusion Proteins with Peptide Fragments Derived from the ATSα

The C-terminal acidic tail of α-synuclein (ATSα) is composed of 45 amino acids (residues 96–140), and 15 Glu/Asp residues are scattered throughout the ATSα region. The present inventors examined whether deletion mutants of GST-synuclein fusion proteins with peptide fragments derived from the ATSα are heat resistant. For this, a series of GST-ATSα deletion mutants were constructed by ligating the gene part of the ATSα of α-synuclein into pGEX vector. DNAs encoding the part of the ATSα were synthesized with olignucleotides described in Table 4 (SEQ ID NOS:20–27) using an automatic DNA synthesizer.

TABLE 4

| Primer | | Sequence |
|---|---|---|
| 10 | Sense | GATCCAATGAAGAAGGAGCCCCACAGGAAGGCATTCTGGAAGATTAAG (SEQ ID NO:20) |
| 11 | Antisense | AATTCTTAATCTTCCAGAATGCCTTCCTGTGGGGCTCCTTCTTCATTG (SEQ ID NO:21) |
| 12 | Sense | GATCCGAAGATATGCCTGTAGATCCTGACAATGAGGCTTATGAATAAG (SEQ ID NO:22) |
| 13 | Antisense | AATTCTTATTCATAAGCCTCATTGTCAGGATCTACAGGCATATCTTCG (SEQ ID NO:23) |
| 14 | Sense | GATCCGATCCTGACAATGAGGCTTATGAAATGCCTTCTGAGGAAGGGTATCAAGACTACGAACCTGAAGCCTAAG (SEQ ID NO:24) |
| 15 | Antisense | AATTCTTAGGCTTCAGGTTCGTAGTCTTGATACCCTTCCTCAGAAGGCATTTCATAAGCCTCATTGTCAGGATCG (SEQ ID NO:25) |
| 16 | Sense | GATCCGAGGAAGGGTATCAAGACTACGAACCTGAAGCCTAAG (SEQ ID NO:26) |
| 17 | Antisense | AATTCTTAGGCTTCAGGTTCGTAGTCTTGATACCCTTCCTCG (SEQ ID NO:27) |

Figure 10A:
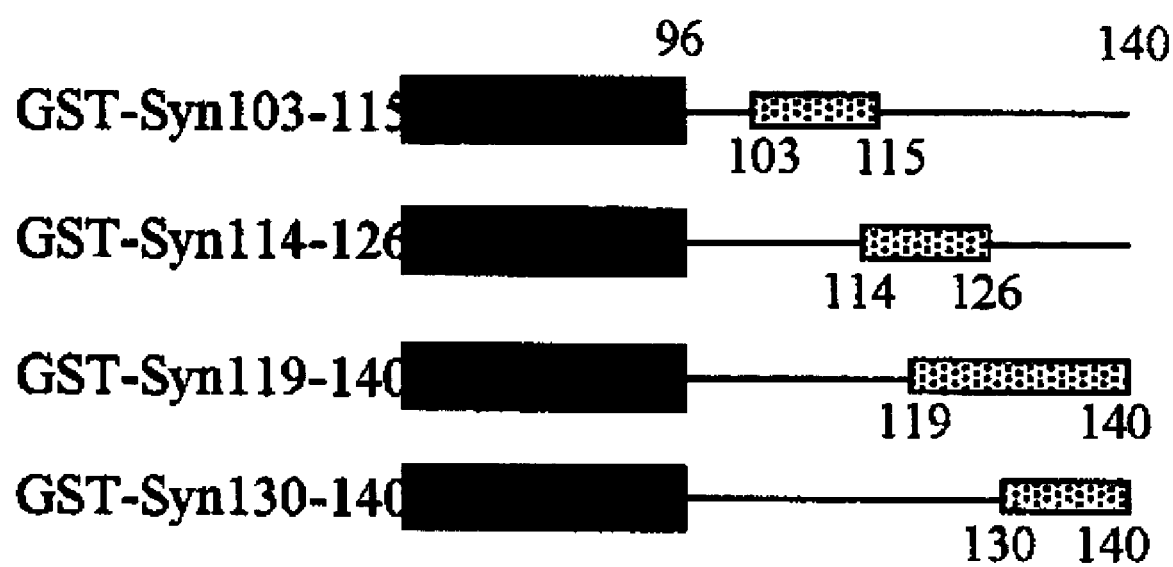
FIG. 10A is a schematic diagram of the GST-synuclein fusion protein containing peptides composed of amino acids of the C-terminal acidic tail region of α-synuclein (ATSα; Syn96–140)

GST-Syn103–115 was constructed using an oligonucleotide of SEQ ID NO:20 as sense and oligonucleotide of SEQ ID NO:21 as antisense. GST-Syn114–126 was constructed using oligonucleotides represented by SEQ ID NO:22 and SEQ ID NO:23. GST-Syn119–140 was constructed using oligonucleotides represented by SEQ ID NO:24 and SEQ ID NO:25. GST-Syn130–140 was constructed using oligonucleotides represented by SEQ ID NO:26 and SEQ ID NO:27. The synthesized sense and antisense DNA pairs were annealed and ligated into BamHI and EcoRI restriction sites of the pGEX vectors to construct a series of expression vectors of GST-ATSα deletion mutants (FIG. 10A), as follows: GST-Syn103–115 containing 13 amino acids of ATSα (residues 103–115); GST-Syn114–126 containing 13 amino acids of ATSα (residues 114–126); GST-Syn119–140 containing 22 amino acids of ATSα (residues 119–140); and GST-Syn130–140 containing 11 amino acids of ATSα (residues 13–140). All the expression vectors (pGST-Syn103–115, pGST-Syn114–126, pGST-Syn119–140 and pGST-Syn130–140) were verified for their sequences by DNA sequencing. The expression vectors pGST-Syn103–115, pGST-Syn114–126, pGST-Syn119–140 and pGST-Syn130–140 were transformed into the E. coli BL21 (DE3) and the resulting recombinant proteins were purified by affinity chromatography using glutathione-Sepharose 4B beads. The GST-ATSα fusion proteins were further purified on an FPLC gel-filtration column.

The GST-ATSα fusion proteins were examined for heat-resistance. Each protein suspended in PBS (0.2 mg/ml) was heated in boiling water baths for 10 minutes and cooled in the air. The protein samples were centrifuged at 15,000 rpm for 10 minutes and the supernatants were analyzed on a 12% SDS polyacrylamide gel. The protein bands on the SDS polyacrylamide gel were stained with Coomassie Brilliant blue R250 to be visible.

Figure 10B:
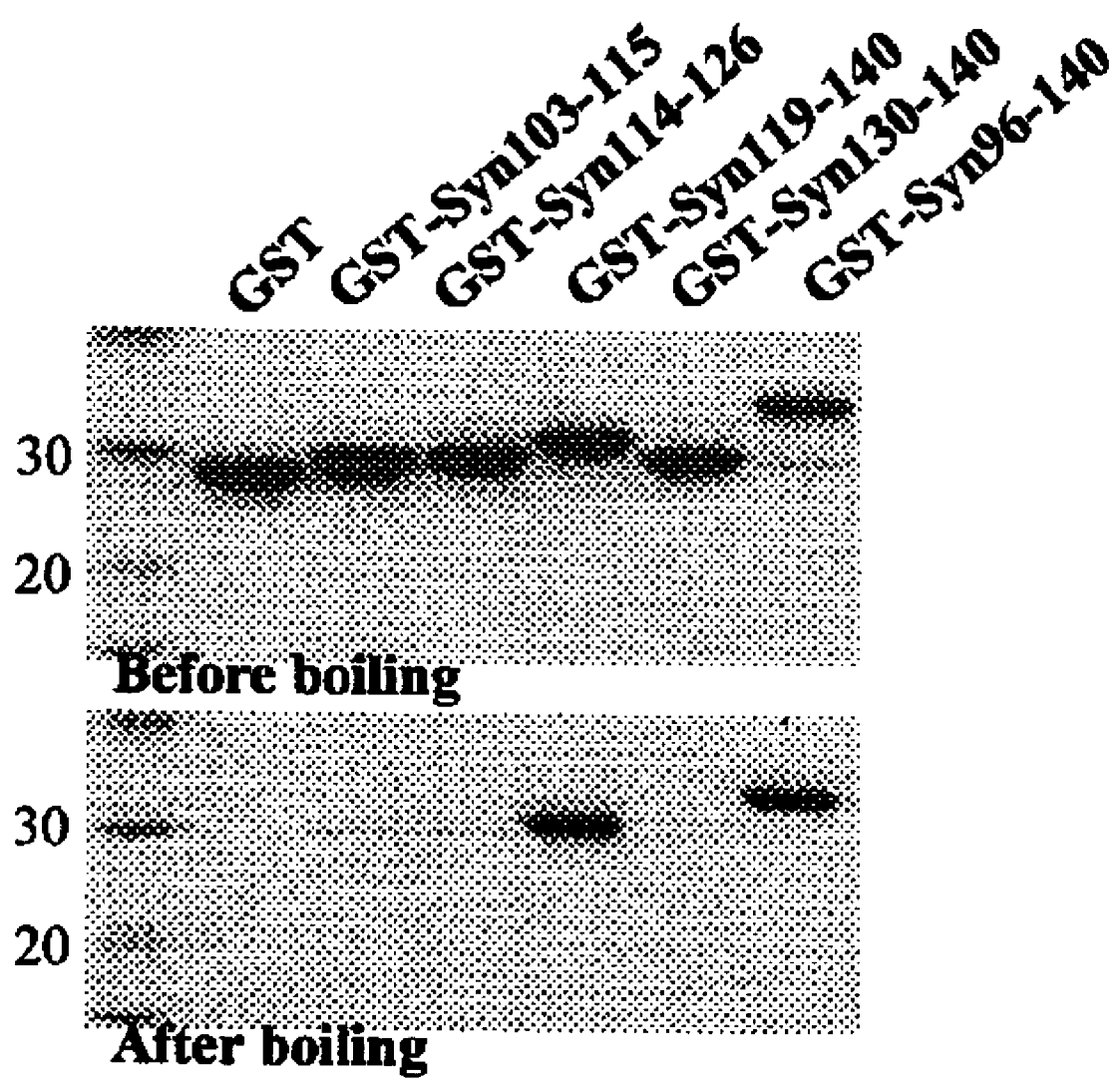
FIG. 10B is the results of SDS-PAGE showing thermal behaviors of the GST-ATSα fusion protein deletion mutants containing peptides derived from the ATSα at the concentration of 0.6 mg/ml before (the upper panel) and after (the lower panel) boiling.

As shown in FIG. 10B, when these deletion mutants of the GST-ATSα fusion proteins were thermally treated at a high concentration (0.6 mg/ml), GST-Syn96–140 containing the entire region of ATSα and GST-Syn119–140 containing 22 amino acids of ATSα did not precipitate at all, while GST-Syn103–115, GST-Syn114–126 and GST-Syn130–140 containing 11–13 amino acids partially precipitated. On the other hand, when these deletion mutants of the GST-ATSα fusion proteins were thermally treated at a low concentration (0.2 mg/ml), none of the proteins aggregated (data not shown).

Figure 10C:
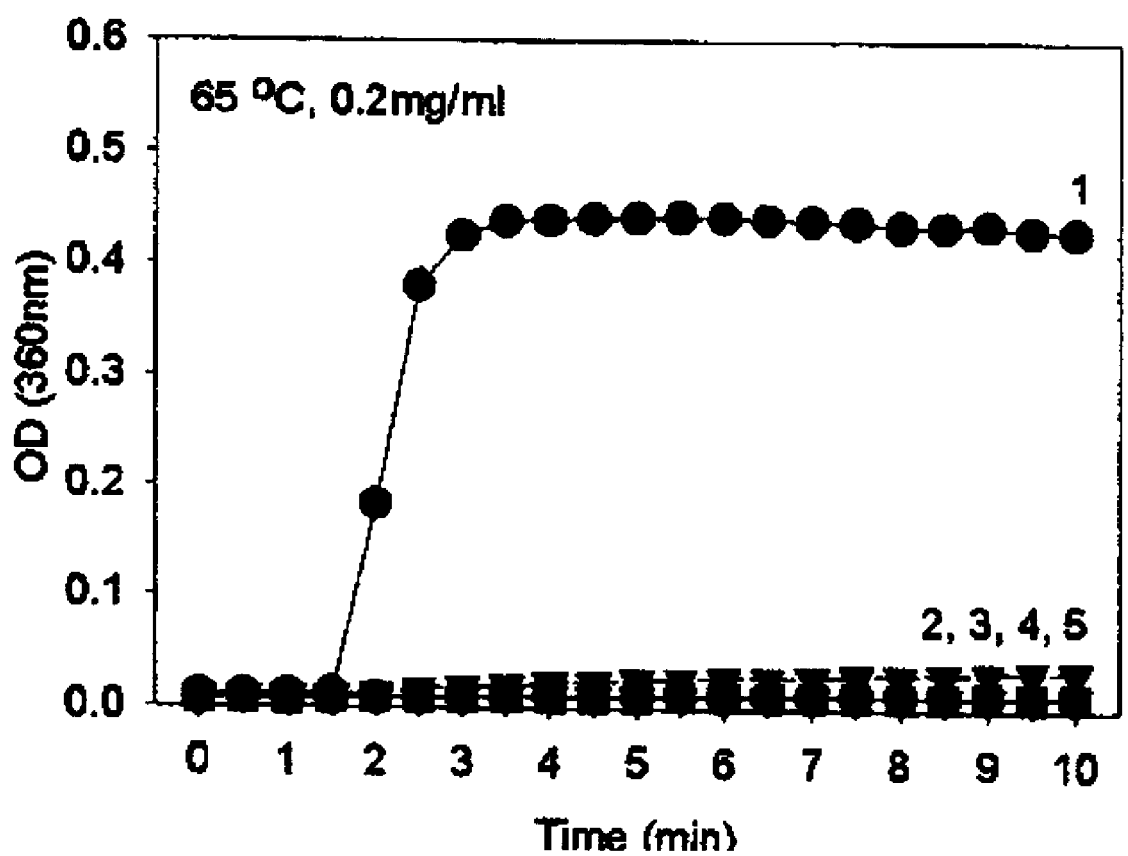
FIG. 10C is a graph of absorbance showing aggregation of the GST-ATSα fusion protein deletion mutants induced by heat treatment at 65° C. at the concentration of 0.2 mg/ml (1: GST, 2: GST-Syn103–115, 3: GST-Syn114–126, 4: GST-Syn130–140, 5: GST-Syn119–140)
Figure 10D:
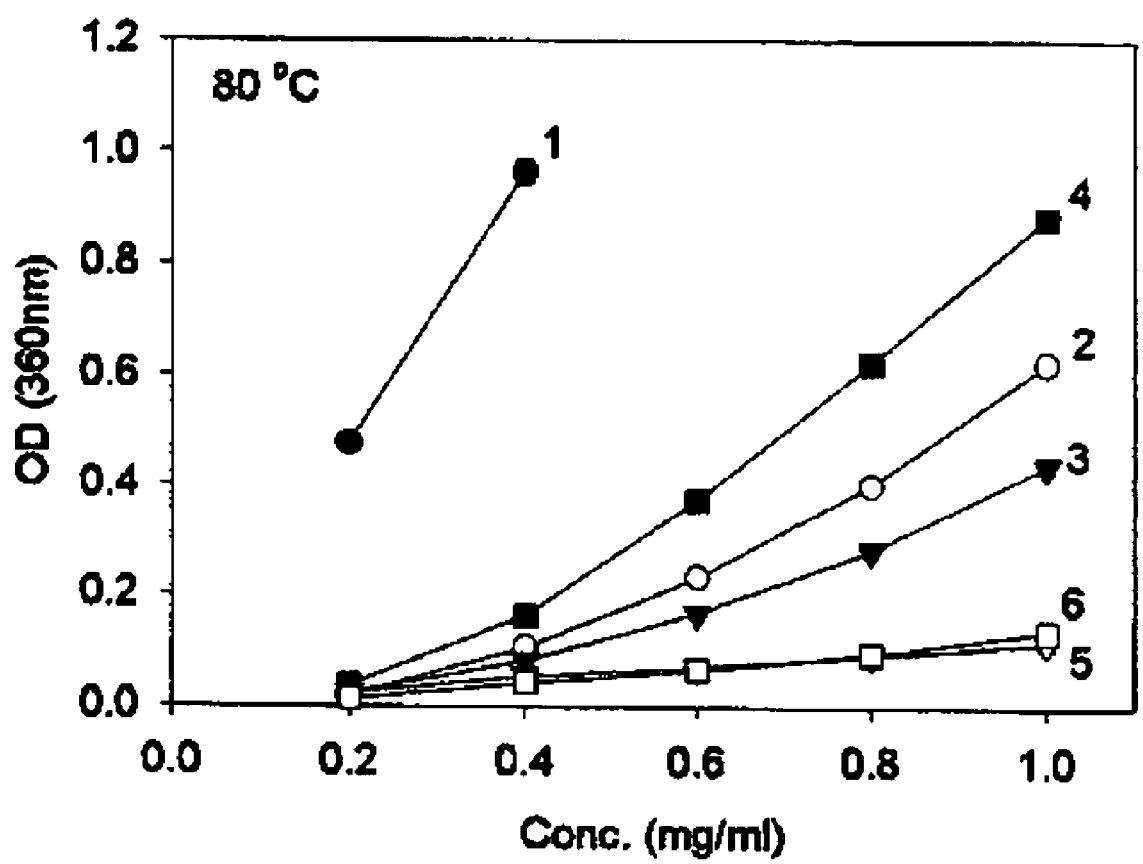
FIG. 10D is a graph of absorbance showing aggregation of the GST-ATSα fusion protein deletion mutants induced by heat treatment at 80° C. for 10 minutes at a concentration in the range of 0.2 mg/ml to 1.0 mg/ml (1: GST, 2: GST-Syn103–115, 3: GST-Syn114–126, 4: GST-Syn130–140, 5: GST-Syn119–140, 6: GST-Syn96–140)

Also, the thermal behaviors of GST-ATSα deletion mutants were quantitatively analyzed by monitoring absorbance at 360 nm according to time while setting the concentration of each protein at 0.2 mg/ml at 65° C. (Lee G. J. and Vierling E., Method Enzymol., 290, 360–65 (1998); and Horwitz J. Proc. Natl. Acad. Sci. USA 89, 10449–53 (1992)). In the experiment, as shown in FIG. 10C, the $OD_{360}$ of the GST protein drastically increased 2 minutes after heat treatment, and most of the protein had aggregated by 3 minutes. In contrast, the GST-ATSα deletion mutants did not aggregate at all even 10 minutes after heat treatment. Next, the GST-ATS α deletion mutants were qualitatively assayed by monitoring the absorbance at 360 nm while varying the concentration from 0.2 mg/ml to 1.0 mg/ml after heat treatment at 80° C. for 10 minutes. As shown in FIG. 10D, GST-5Syn96–140 containing the entire region of ATSα and GST-Syn119–140 containing 22 amino acids of ATSα did not precipitate at all after heat treatment regardless of the concentration, while GST-Syn103–115, GST-Syn114–126 and GST-Syn130–140 containing 11–13 amino acids did not precipitate at all at a low concentration but increasingly aggregated as the concentration was raised. It is noted that the aggregation of protein is proportional to the concentration. Thus, it is demonstrated that the deletion mutants of the GST-ATSα fusion protein have heat resistance superior to that of wild type GST and the heat resistance interestingly varies according to the length of ATSα. Therefore, optimum effects can be achieved by suitably selecting the length of ATSα according to the size and property of a target protein.

Example 13

Heat Resistance of GST-synuclein Fusion Protein Containing the C-Terminal Acidic Tail Region of β-Synuclein or γ-Synuclein In addition to α-synuclein, β-synuclein and γ-synuclein, found in human, are proteins constituting the synuclein family, and share a high homology in their amino acid sequences with each other. Particularly, the N-terminal amphipathic region of synuclein is strictly conserved among the synuclein family members from the Torpedo to humans. However, the C-terminal acidic tails of the synuclein family members are very diverse in size as well as in sequence (Lavedan C., Genome Research, 8, 871–880 (1998); Lucking C. B. and Brice A. Cell Mol Life Sci, 57, 1894–1908 (2000); Iwai A., Biochem. Biophys. Acta, 1502, 95–109 (2000); and Hashimoto M. and Masliah E. Brain Pathol. 9, 707–720 (1999)). The present inventors examined whether GST-ATSβ and GST-ATSγ fusion proteins containing the acidic tails of β-synuclein (ATSβ) and γ-synuclein (ATSγ), respectively, are heat resistant.

GST-ATSβ and GST-ATSγ fusion proteins were prepared by subcloning the ATSβ (residues 85–134) and ATSγ (residues 96–127), respectively, into pGEX vector. The protein coding region of the ATSβ was amplified by PCR with 5'oligonucleotide primer (SEQ ID NO:28) containing the underlined BamHI restriction site and 3'-oligonucleotide primer (SEQ ID NO:29) containing the underlined XhoI restriction site. The protein coding region of the ATSγ was amplified by PCR with the 5'oligonucleotide primer (SEQ ID NO:30) containing the underlined BamHI restriction site and 3' oligonucleotide primer (SEQ ID NO:31) containing the underlined EcoRI restriction site.

TABLE 5

| Primer | | Sequence |
|---|---|---|
| 18 | Sense | AGCTAA<u>GGATCC</u>AAGAGGGAGGAATTCC (SEQ ID NO:28) |
| 19 | Antisense | AAGTAA<u>CTCGAG</u>CTACGCCTCTGGCTCATA (SEQ ID NO:29) |
| 20 | Sense | AAGAATGGATCCCGCAAGGAGGACTTGA (SEQ ID NO:30) |
| 21 | Antisense | AATAGCGAATTCCTAGTCTCCCCCACTCT (SEQ ID NO:31) |

The amplified DNAs were gel purified, digested with appropriate enzymes, then ligated into the pGEX vector which had been digested with appropriate restriction enzymes and gel purified. All expression vectors (pGST-ATSβ and pGST-ATSγ were verified for their sequences by DNA sequencing. The expression vectors were transformed into the E. coli strain, BL21 (DE3), and the recombinant GST-synuclein fusion proteins (GST-ATSβ and GST-ATSγ) were purified by affinity chromatography using glutathione-Sepharose 4B beads. The GST-ATS fusion proteins were further purified on an FPLC gel-filtration column.

GST-ATSβ and GST-ATSγ fusion proteins were examined for heat-resistance as in Example 6. Each protein suspended in PBS (0.6 mg/ml) was heated in boiling water baths for 10 minutes and cooled in the air. The protein samples were centrifuged at 15,000 rpm for 10 minutes and the supernatants were analyzed on a 12% SDS polyacrylamide gel. The protein bands on the SDS polyacrylamide gel were stained with Coomassie Brilliant blue R250.

Figure 11A:
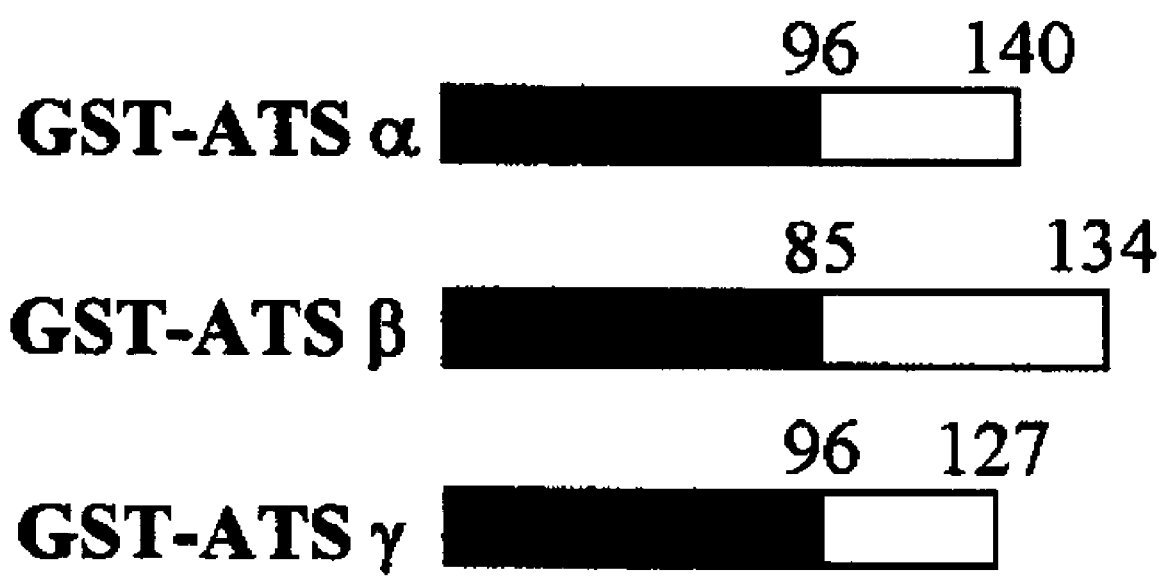
FIG. 11A is a schematic diagram of the GST-synuclein fusion proteins containing the C-terminal acidic tail region of α-synuclein (ATSα), β-synuclein (ATSβ) and γ-synuclein (ATS γ)
Figure 11B:
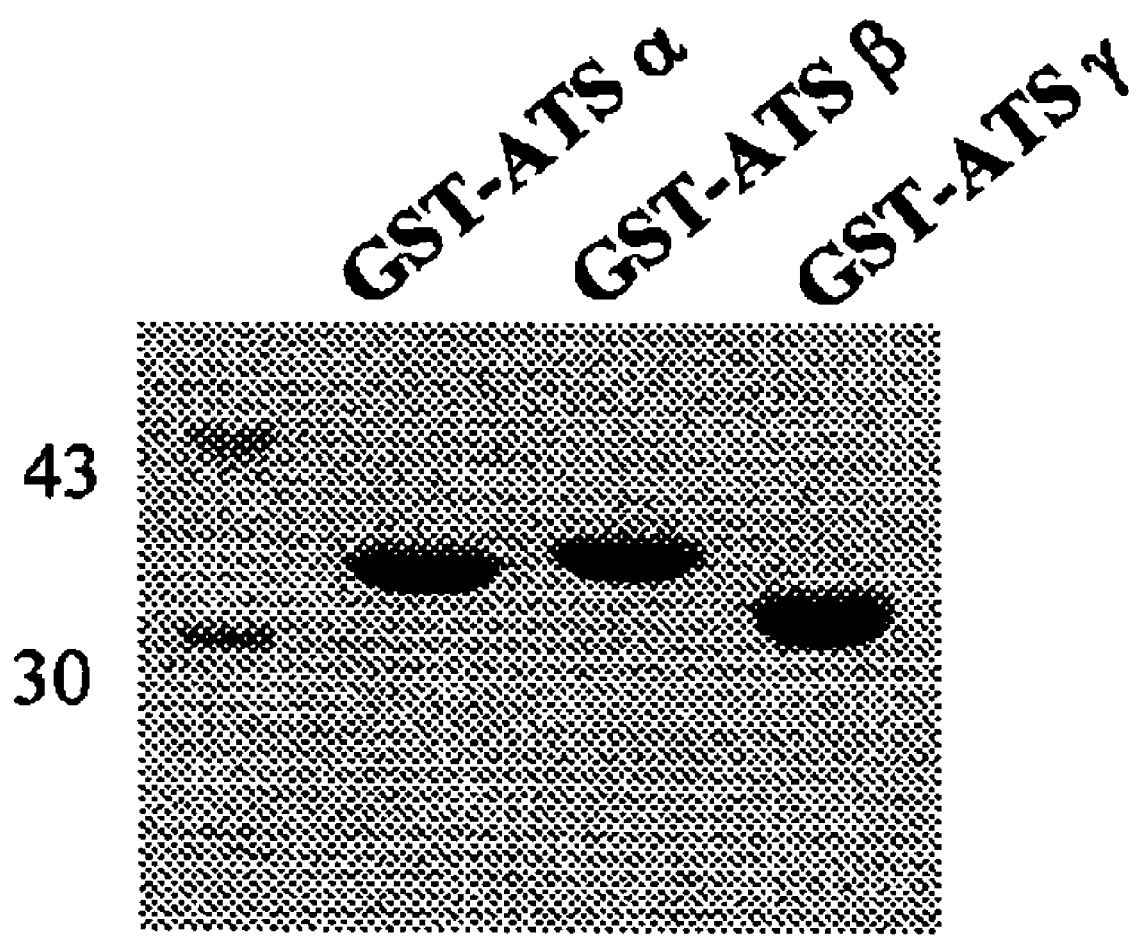
FIG. 11B is the results of SDS-PAGE showing thermal behaviors of the GST-ATS fusion proteins (GST-ATSα, GST-ATSβ and GST-ATSγ) after boiling for 10 minutes at the concentration of 0.6 mg/ml.

As shown in FIG. 11B, GST-ATSβ and GST-ATSγ as well as GST-ATSα show protein bands after heat treatment, which indicates that they are not precipitated. Therefore, it is demonstrated that the GST-ATSβ and GST-ATSγ fusion proteins have a high heat resistance.

Figure 11C:
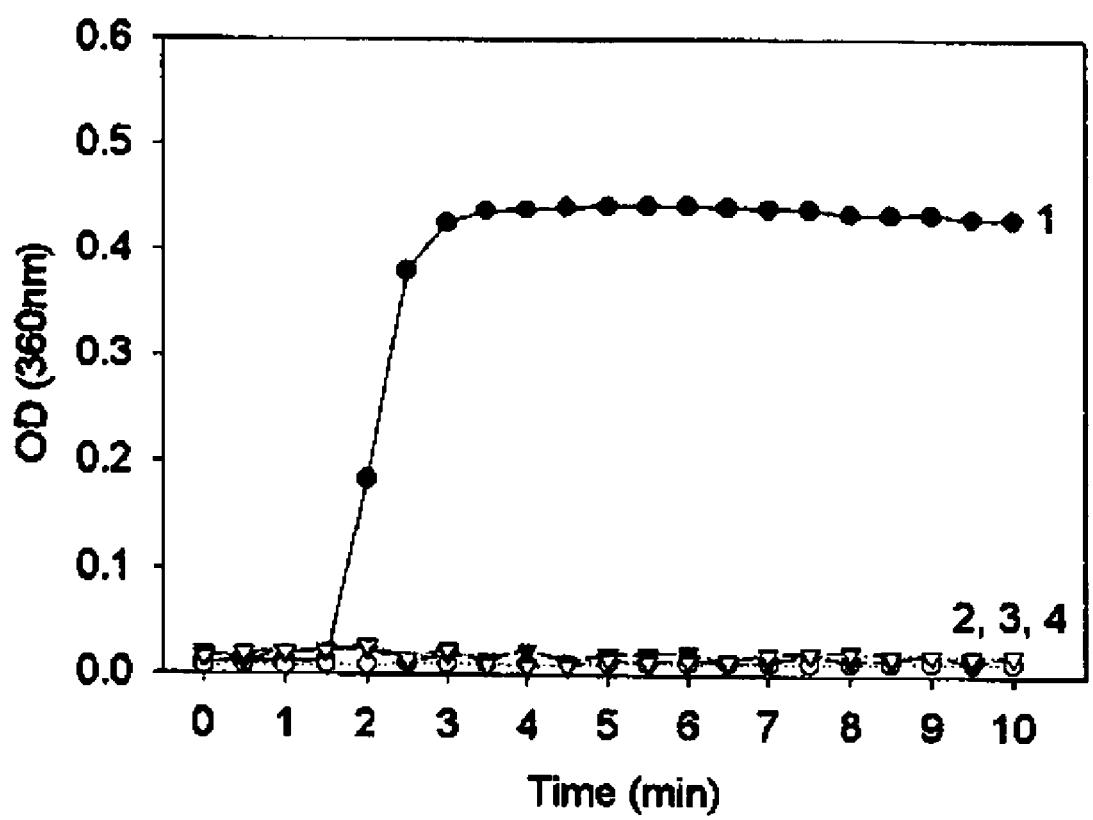
FIG. 11C is a graph of absorbance showing aggregation of the GST-ATS fusion proteins induced by heat treatment at 65° C. at the concentration of 0.2 mg/ml (1: GST, 2: GST-ASTα, 3: GST-ATSβ, 4: GST-ATSγ)
Figure 11D:
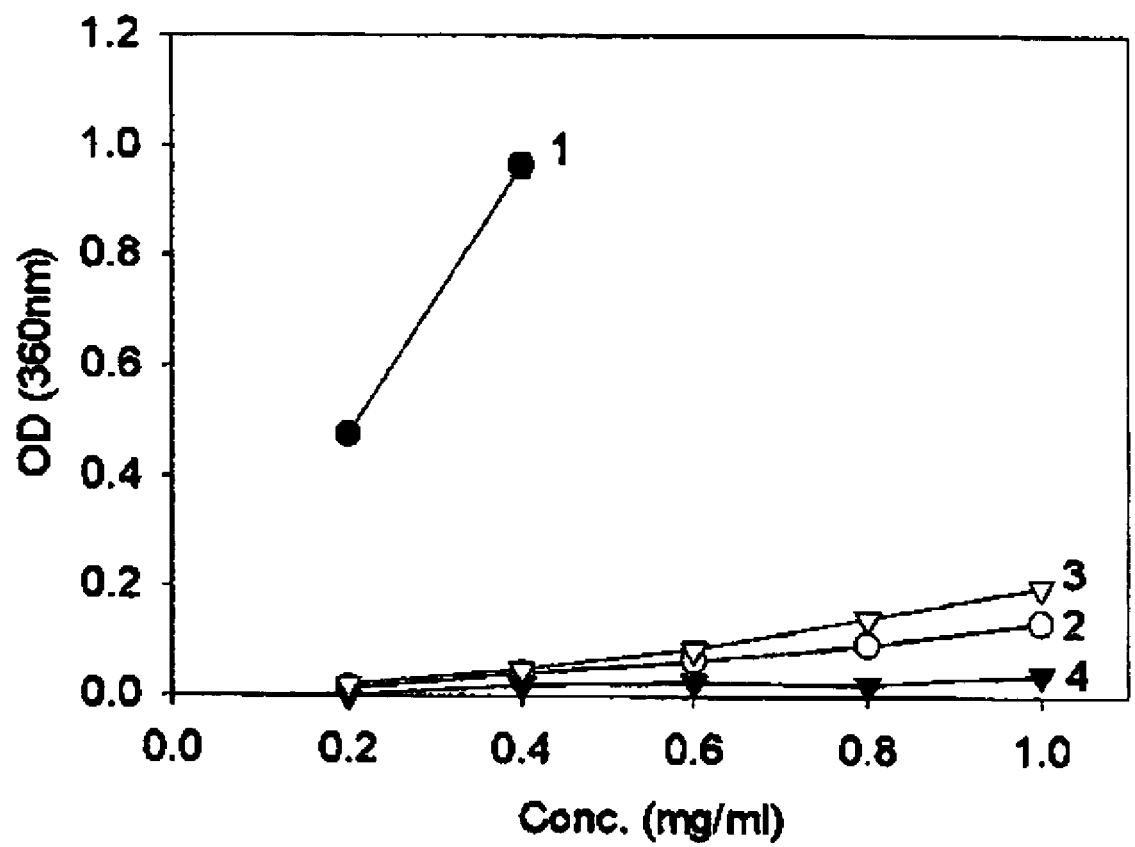
FIG. 11D is a graph of absorbance showing aggregation of the GST-ATS fusion proteins induced by heat treatment at 80° C. for 10 minutes at a concentration in the range of 0.2 mg/ml to 1.0 mg/ml (1: GST, 2: GST-ASTα, 3: GST-ATSβ, 4: GST-ATSγ)

Also, the thermal behaviors of the above GST-ATS fusion proteins were quantitatively assayed by monitoring absorbance at 360 nm according to time while setting the concentration of each protein at 0.2 mg/ml at 65° C. (Lee G. J. and Vierling E., Method Enzymol., 290, 360–65 (1998); and Horwitz J. Proc. Natl. Acad. Sci. USA 89, 10449–53 (1992)). In the experiment, as shown in FIG. 11C, the GST protein had almost aggregated after 2 to 3 minutes. In contrast, the above GST-ATS fusion proteins did not aggregate at all even 10 minutes after heat treatment. Next, the above GST-ATS fusion proteins were qualitatively assayed by monitoring the absorbance at 360 nm while varying the concentration from 0.2 mg/ml to 1.0 mg/ml after heat treatment at 80° C. for 10 minutes. As shown in FIG. 11D, the above GST-ATS fusion proteins did not precipitate at all after heat treatment regardless of the concentration, while the GST protein is completely precipitated at a low concentration. Thus, it is demonstrated that in addition to ATSα, the ATSβ and ATSγ are peptides capable of providing heat resistance to other proteins and they can be used in preparation of fusion proteins having resistance to environmental stresses. Also, it is presumed that since the amino acid sequence of synoretin is very similar to that of γ-synuclein, the acidic tail of synoretin may be similarly used.

Example 14

Heat-resistance of GST-polyglutamate Fusion Proteins Containing the Acidic Tail Composed of Polyglutamate In the C-terminal acidic tail region of synuclein, a number of negatively charged amino acid residues such as Glu/Asp residues are characteristically scattered therethrough. The present inventors finally examined whether GST-polyglutamate fusion proteins with genuinely negatively charged peptide fragments such as polyglutamate have heat resistance. For this, a series of GST-polyglutamate fusion proteins were constructed by ligating the gene part of polyglutamate into pGEX vector (FIG. 12A). DNAs encoding the part of the polyglutamate peptide were synthesized using an automatic DNA synthesizer (Table 6, SEQ ID NOS: 32–35). The oligonucleotides of SEQ ID NOS:32 and 33 were sense and antisense DNAs to synthesize GST-E5 (containing 5 glutamate residues), respectively and the oligonucleotides of SEQ ID NOS:34 and 35 were sense and antisense DNAs to synthesize GST-E10 (containing 10 glutamate residues). The synthesized sense and antisense DNA pairs were annealed and the polyglutamate gene parts were ligated into BamHI and EcoRI restriction sites of the pGEX vectors to construct a series of expression vectors directing GST-polyglutamate fusion proteins. All the expression vectors (pGST-E5 and pGST-E10) were verified for their sequences by DNA sequencing.

Table 6

| Primer | | Sequence |
|---|---|---|
| 22 | Sense | GATCCGAAGAAGAAGAAGAATAA (SEQ ID NO:32) |
| 23 | Anti-sense | AATTCTTATTCTTCTTCTTCTTCG (SEQ ID NO:33) |
| 24 | Sense | GATCCGAAGAAGAAGAAGAAGAAGAAGAAGAAGAAT AAG(SEQ ID NO:34) |
| 25 | Anti-sense | AATTCTTATTCTTCTTCTTCTTCTTCTTCTTCTTCG (SEQ ID NO:35) |

Figure 12B:
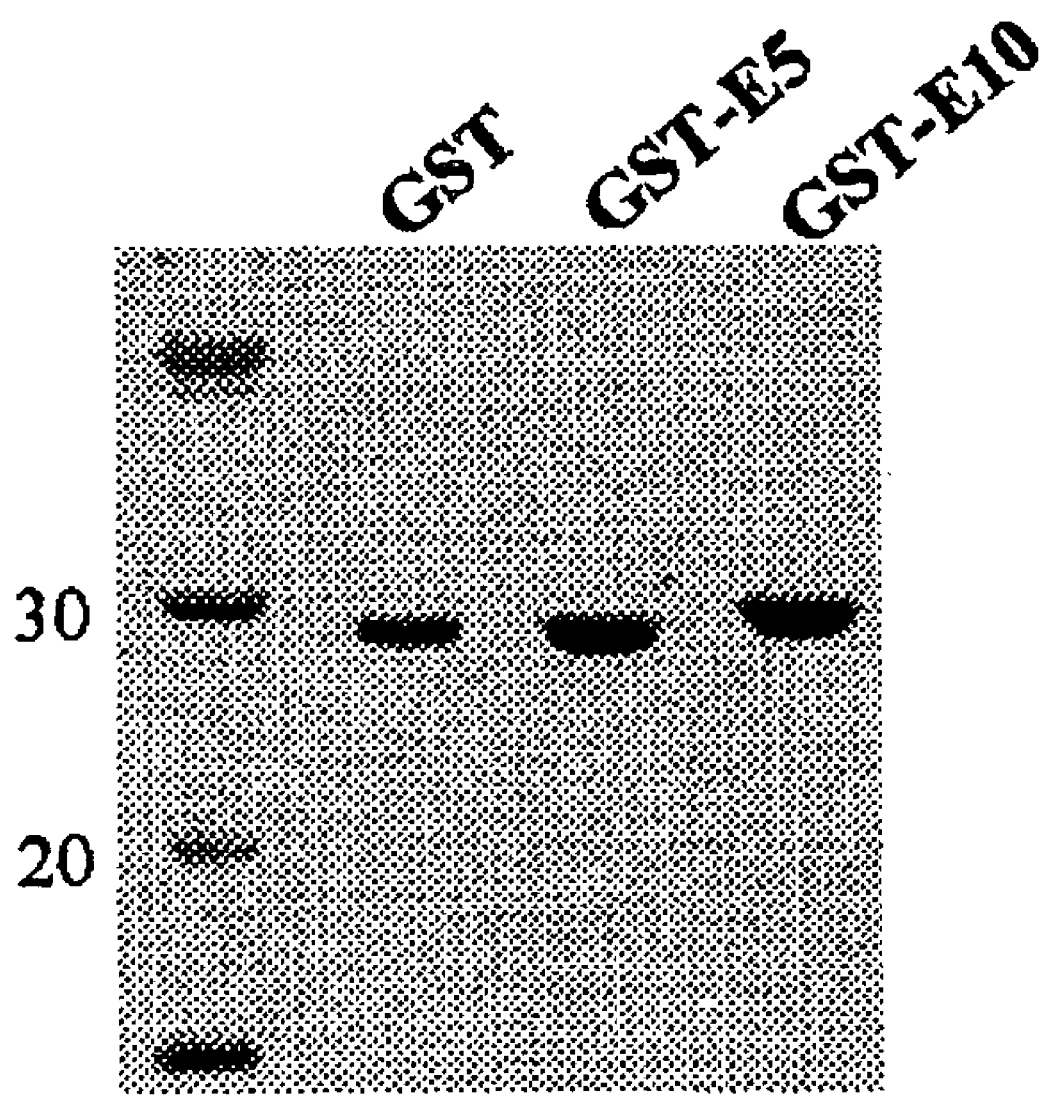
FIG. 12B is the results of SDS-PAGE analysis of the purified GST-E5 and GST-E10 fusion proteins.

The expression vectors pGST-E5 and pGST-E10 were transformed into the *E. coli* BL21 (DE3). The resulting recombinant proteins were purified by affinity chromatography using glutathione-Sepharose 4B beads. The GST-polyglutamate fusion proteins were further purified on an FPLC gel-filtration column (FIG. 12B). The GST-polyglutamate fusion proteins were prepared and purified following the method as described in Example 7 and examined for their heat resistance. Each protein suspended in PBS (0.6 mg/ml) was heated in boiling water baths for 10 minutes and cooled in the air. The protein samples were centrifuged at 15,000 rpm for 10 minutes and the supernatants were analyzed on a 12% SDS polyacrylamide gel. Both GST-E5 and GST-E10 did not show protein bands after heat treatment, which indicates that they had been completely precipitated by heat treatment. Therefore, it is demonstrated that the GST-E5 and GST-E10 do not have heat resistance at such stringent conditions.

Figure 12C:
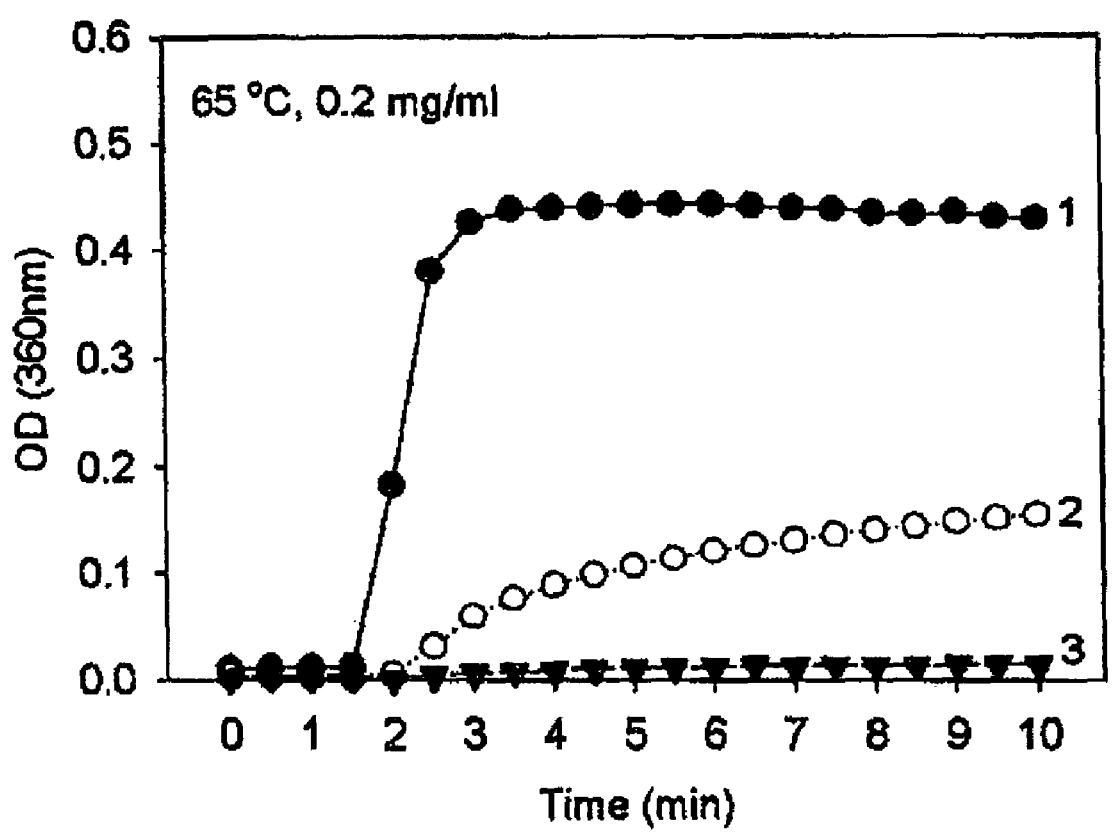
FIG. 12C is a graph of absorbance showing aggregation of the GST-E5 and GST-E10 fusion proteins induced by heat treatment at 65° C. at the concentration of 0.2 mg/ml as a function of time (1: GST, 2: GST-E5, 3: GST-E10)
Figure 12D:
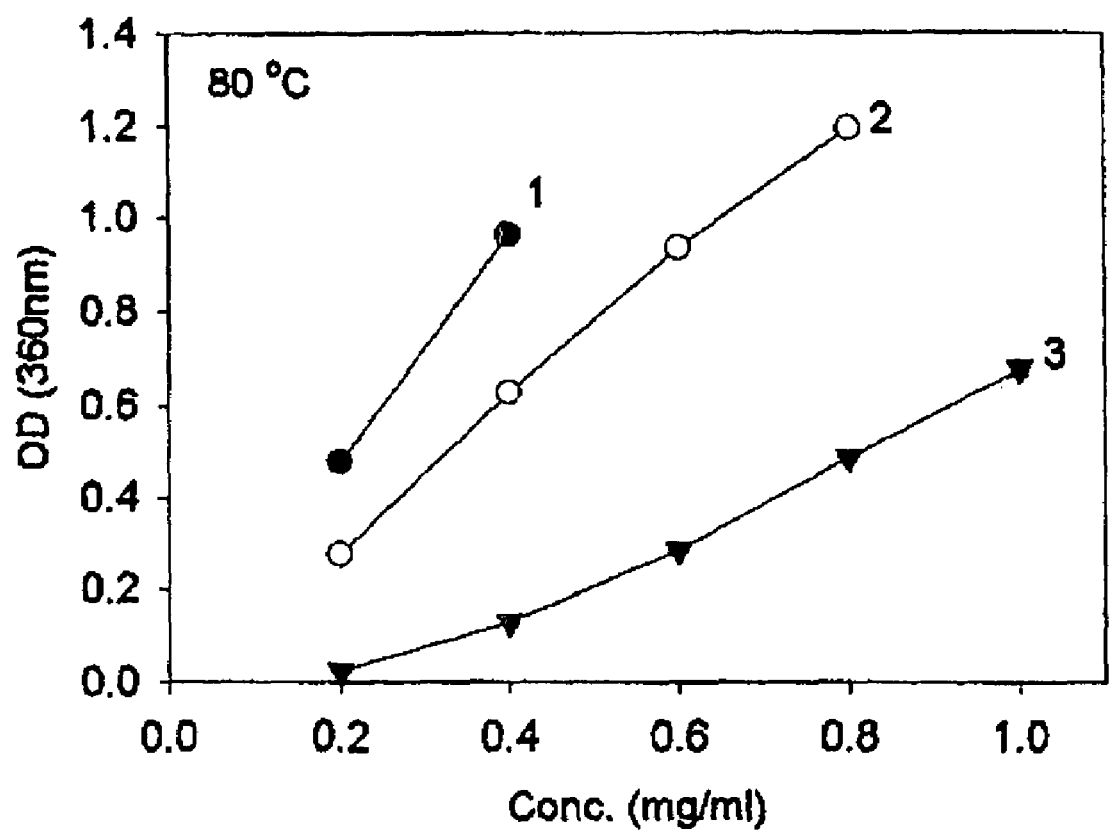
FIG. 12D is a graph of absorbance showing aggregation of the GST-E5 and GST-E10 fusion proteins induced by heat treatment at 80° C. for 10 minutes at a concentration in the range of 0.2 mg/ml to 1.0 mg/ml (1: GST, 2: GST-E5, 3: GST-E10).

Also, the thermal behaviors of the above GST-E5 and GST-E10 fusion proteins were quantitatively assayed by monitoring absorbance at 360 nm according to time while setting the concentration of each protein at 0.2 mg/ml at 65° C. (Lee G. J. and Vierling E., Method Enzymol., 290, 360–65 (1998); and Horwitz J. Proc. Natl. Acad. Sci. USA 89, 10449–53 (1992)). In the experiment, as shown in FIG. 12C, the GST protein were almost aggregated after 2 to 3 minutes and the GST-E5 fusion protein were aggregated in a considerable amount under the same conditions, whereas the GST-E10 fusion protein did not aggregate at all even after heat treatment for 10 minutes at 65° C. Next, the GST-polyglutamate fusion proteins were quantitatively assayed by monitoring the absorbance at 360 nm while varying the concentration from 0.2 mg/ml to 1.0 mg/ml after heat treatment at 80° C. for 10 minutes. As shown in FIG. 12D, the GST protein is completely precipitated at a low concentration and most of the GST-E5 protein was precipitated at a high concentration. In contrast, the GST-E10 protein was partially precipitated after heat treatment under the same conditions and increasingly aggregated as the concentration was raised. Thus, it is noted that as the length of polyglutamate increases, the negative charge considerably increases and thereby, aggregation decreases. However, interestingly, it is noted that the polyglutamate tail is considerably less effective to provide heat resistance, as compared to ATS peptides containing the same number of glutamate residues. In fact, GST-Syn130–140 shows heat resistance far superior to GST-E5 containing the same number of glutamate residues and even slightly higher than that of GST-E10 containing two times more glutamate residues (compare FIG. 10D with FIG. 12D). Therefore, it is suggested that the characteristic amino acid sequence of ATS, in addition to the increased solubility of proteins due to the increase of the negative charge, plays an important role in the mechanism, by which fusion proteins with ATS show high resistance to environmental stresses. Also, the present inventors interestingly observed that a fusion protein containing a positively charged peptide such as polyarginine does not show heat resistance at all (data not shown), which supports that the characteristic amino acid sequence of ATS plays a very important role in providing resistance to environmental stresses.

As described above, according to the present invention, peptides of the C-terminal acidic tail of synuclein family (ATS), or peptides comprising at least one sequence selected from the group consisting of oligopeptide sequences of at least about 10 but not more than about 50 continuous amino acid residues in the amino acid sequence of the C-terminal acidic tail of synuclein family (ATS), or fusion proteins with environmental stress resistance formed by fusing the said peptides to fusion partner proteins show resistance to various environmental stresses while conserving the intrinsic properties of the fusion partner proteins and are thus expected to be usefully applied in many industrial fields such as medical science, bioengineering, food, etc.

What is claimed is:

1. A nucleic acid encoding a peptide with environmental stress resistance selected from the group consisting of amino acid residues 103–115, amino acid residues 114–126, amino acid residues 119–140 and amino acid residues 130–140 of C-terminal acidic tail of α-synuclein, amino acid residues 85–134 of the C-terminal acidic tail of β-synuclein, amino acid residues 96–127 of the C-terminal acid tail of γ-synuclein and amino acid residues 96–127 of the C-terminal acidic tail of synoretin.

2. The nucleic acid according to claim 1, wherein the synuclein is of human origin.

3. The nucleic acid according to claim 1, wherein the environmental stress is heat, pH or metals.

4. A recombinant vector comprising the nucleotide sequence of claim 1.

5. A host cell transformed or transfected with the recombinant vector of claim 4.

6. A method for preparing a peptide with environmental stress resistance comprising culturing the host cell according to claim 5 to produce the peptide and isolating the peptide.

7. A nucleic acid encoding a fusion protein comprising a peptide with environmental stress resistance selected from the group consisting of amino acid residues 103–115, amino acid residues 114–126, amino acid residues 119–140 and amino acid residues 130–140 of C-terminal acidic tail of α-synuclein, amino acid residues 85–134 of the C-terminal acidic tail of β-synuclein, amino acid residues 96–127 of the C-terminal acid tail of γ-synuclein and amino acid residues 96–127 of the C-terminal acidic tail of synoretin and a fusion partner protein.

8. The nucleic acid according to claim 7, wherein the peptide binds to a position of an amino acid residue that does not affect the intrinsic properties of the fusion partner protein.

9. The nucleic acid according to claim 7, wherein the position of the amino acid residue is the N-terminus and/or the C-terminus of the fusion partner protein.

10. The nucleic acid according to claim 7, wherein the fusion partner protein is a protein which is unstable to environmental stress.

11. The nucleic acid according to claim 7, wherein the protein which is unstable to environmental stress is glutathione-S-transferase or dihydrofolate reductase.

12. A recombinant vector comprising the nucleotide sequence of claim 7.

13. An isolated host cell transformed or transfected with the recombinant vector of claim 12.

14. A method for preparing fusion protein showing environmental stress resistance while conserving intrinsic properties of the protein unstable to environmental stress, which comprises culturing the host cell according to claim 13 to produce the fusion protein and isolating the fusion protein.

* * * * *

SEQUENCE LISTING

<160> NUMBER OF SEQ ID NOS: 37

<210> SEQ ID NO 1
<211> LENGTH: 45
<212> TYPE: PRT
<213> ORGANISM: Homo sapiens
<220> FEATURE:
<221> NAME/KEY: PEPTIDE
<222> LOCATION: (1)..(45)
<223> OTHER INFORMATION: Acidic tail amino acid sequence 96-140 of
      alpha-synuclein

<400> SEQUENCE: 1

Lys Lys Asp Gln Leu Gly Lys Asn Glu Glu Gly Ala Pro Gln Glu Gly
1               5                   10                  15

Ile Leu Glu Asp Met Pro Val Asp Pro Asp Asn Glu Ala Tyr Glu Met
            20                  25                  30

Pro Ser Glu Glu Gly Tyr Gln Asp Tyr Glu Pro Glu Ala
        35                  40                  45

<210> SEQ ID NO 2
<211> LENGTH: 50
<212> TYPE: PRT
<213> ORGANISM: Homo sapiens
<220> FEATURE:
<221> NAME/KEY: PEPTIDE
<222> LOCATION: (1)..(50)
<223> OTHER INFORMATION: Acidic tail amino acid sequence 85-134 of
      beta-synuclein

<400> SEQUENCE: 2

Lys Arg Glu Glu Phe Pro Thr Asp Leu Lys Pro Glu Glu Val Ala Gln
1               5                   10                  15

Glu Ala Ala Glu Glu Pro Leu Ile Glu Pro Leu Met Glu Pro Glu Gly
            20                  25                  30

Glu Ser Tyr Glu Asp Pro Pro Gln Glu Glu Tyr Gln Glu Tyr Glu Pro
        35                  40                  45

Glu Ala
    50

<210> SEQ ID NO 3
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Acidic tail amino acid sequence 96-127 of
      gamma-synuclein

<400> SEQUENCE: 3

Ala Lys Glu Asp Leu Arg Asp Ser Ala Pro Gln Gln Glu Gly Val Ala
1               5                   10                  15

Ser Lys Glu Lys Glu Glu Val Ala Glu Glu Ala Gln Ser Gly Gly Asp
            20                  25                  30

<210> SEQ ID NO 4
<211> LENGTH: 32
<212> TYPE: PRT
<213> ORGANISM: Homo sapiens

```
<220> FEATURE:
<221> NAME/KEY: PEPTIDE
<222> LOCATION: (1)..(32)
<223> OTHER INFORMATION: Acidic tail amino aicd sequence 96-127 of
      synoretin

<400> SEQUENCE: 4

His Lys Glu Ala Leu Lys Gln Pro Val Pro Ser Gln Glu Asp Glu Ala
1               5                   10                  15

Ala Lys Ala Glu Glu Gln Val Ala Glu Thr Lys Ser Gly Gly Asp
            20                  25                  30

<210> SEQ ID NO 5
<211> LENGTH: 275
<212> TYPE: PRT
<213> ORGANISM: Artificial Sequence
<220> FEATURE:
<221> NAME/KEY: MISC_FEATURE
<222> LOCATION: (1)..(275)
<223> OTHER INFORMATION: GST-Syn96-140 fusion protein

<400> SEQUENCE: 5

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Glu Ile Trp Met Lys Lys Asp Gln Leu Gly Lys Asn Glu Glu
225                 230                 235                 240

Gly Ala Pro Gln Glu Gly Ile Leu Glu Asp Met Pro Val Asp Pro Asp
                245                 250                 255

Asn Glu Ala Tyr Glu Met Pro Ser Glu Glu Gly Tyr Gln Asp Tyr Glu
            260                 265                 270

Pro Glu Ala
        275
```

<210> SEQ ID NO 6
<211> LENGTH: 308
<212> TYPE: PRT
<213> ORGANISM: Artificial Sequence
<220> FEATURE:
<221> NAME/KEY: MISC_FEATURE
<222> LOCATION: (1)..(308)
<223> OTHER INFORMATION: GST-Syn61-140 fusion protein

<400> SEQUENCE: 6

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser His Met Glu Gln Val Thr Asn Val Gly Gly Ala Val Val Thr
225                 230                 235                 240

Gly Val Thr Ala Val Ala Gln Lys Thr Val Glu Gly Ala Gly Ser Ile
                245                 250                 255

Ala Ala Ala Thr Gly Phe Val Lys Lys Asp Gln Leu Gly Lys Asn Glu
            260                 265                 270

Glu Gly Ala Pro Gln Glu Gly Ile Leu Glu Asp Met Pro Val Asp Pro
        275                 280                 285

Asp Asn Glu Ala Tyr Glu Met Pro Ser Glu Glu Gly Tyr Gln Asp Tyr
    290                 295                 300

Glu Pro Glu Ala
305
```

<210> SEQ ID NO 7
<211> LENGTH: 367
<212> TYPE: PRT
<213> ORGANISM: Artificial Sequence

```
<220> FEATURE:
<221> NAME/KEY: MISC_FEATURE
<222> LOCATION: (1)..(367)
<223> OTHER INFORMATION: GST-Syn1-140 fusion protein

<400> SEQUENCE: 7

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Ala Met Asp Val Phe Met Lys Gly Leu Ser Lys Ala Lys Glu
225                 230                 235                 240

Gly Val Val Ala Ala Ala Glu Lys Thr Lys Gln Gly Val Ala Glu Ala
                245                 250                 255

Ala Gly Lys Thr Lys Glu Gly Val Leu Tyr Val Gly Ser Lys Thr Lys
            260                 265                 270

Glu Gly Val Val His Gly Val Ala Thr Val Ala Glu Lys Thr Lys Glu
        275                 280                 285

Gln Val Thr Asn Val Gly Gly Ala Val Val Thr Gly Val Thr Ala Val
    290                 295                 300

Ala Gln Lys Thr Val Glu Gly Ala Gly Ser Ile Ala Ala Ala Thr Gly
305                 310                 315                 320

Phe Val Lys Lys Asp Gln Leu Gly Lys Asn Glu Glu Gly Ala Pro Gln
                325                 330                 335

Glu Gly Ile Leu Glu Asp Met Pro Val Asp Pro Asp Asn Glu Ala Tyr
            340                 345                 350

Glu Met Pro Ser Glu Glu Gly Tyr Gln Asp Tyr Glu Pro Glu Ala
        355                 360                 365
```

```
<210> SEQ ID NO 8
<211> LENGTH: 829
<212> TYPE: DNA
<213> ORGANISM: Artificial Sequence
<220> FEATURE:
<221> NAME/KEY: misc_recomb
<222> LOCATION: (1)..(829)
<223> OTHER INFORMATION: GST-Syn96-140 fusion protein

<400> SEQUENCE: 8 atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggttccgc gtggatccga gatctggatg aaaaaggacc agttgggcaa gaatgaagaa    720
ggagccccac aggaaggaat tctggaagat atgcctgtgg atcctgacaa tgaggcttat    780
gaaatgcctt cttgaggaag ggtatcaaga ctacgaacct gaagcctaa                829

<210> SEQ ID NO 9
<211> LENGTH: 928
<212> TYPE: DNA
<213> ORGANISM: Artificial Sequence
<220> FEATURE:
<221> NAME/KEY: misc_recomb
<222> LOCATION: (1)..(928)
<223> OTHER INFORMATION: GST-Syn61-140 fusion protein

<400> SEQUENCE: 9 atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggttccgc gtggatctca tatggagcaa gtgacaaatg ttggaggagc agtggtgacg    720
ggtgtgacag cagtagccca agagacagtg gagggagcag ggagcattgc agcagccact    780
ggctttgtca aaaaggacca gttgggcaag aatgaagaag gagccccaca ggaaggaatt    840
```

```
ctggaagata tgcctgtgga tcctgacaat gaggcttatg aaatgccttc ttgaggaagg      900
gtatcaagac tacgaacctg aagcctaa                                         928
```

<210> SEQ ID NO 10
<211> LENGTH: 1105
<212> TYPE: DNA
<213> ORGANISM: Artificial Sequence
<220> FEATURE:
<221> NAME/KEY: misc_feature
<222> LOCATION: (1)..(1105)
<223> OTHER INFORMATION: GST-Syn1-140 fusion protein

<400> SEQUENCE: 10

```
atgtcccta tactaggtta ttggaaaatt aagggccttg tgcaacccac tcgacttctt       60
ttggaatatc ttgaagaaaa atatgaagag catttgtatg agcgcgatga aggtgataaa     120
tggcgaaaca aaaagtttga attgggtttg agtttcccaa tcttccttta ttatattgat     180
ggtgatgtta aattaacaca gtctatggcc atcatacgtt atatagctga caagcacaac     240
atgttgggtg ttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgtttttaaa    540 aaacgtattg aagctatccc acaaattgat aagtacttga atccagcaa gtatatagca     600 tggcctttgc agggctggca agccacgttt ggtggtggcg accatcctcc aaaatcggat     660
ctggttccgc gtggatctgc catggatgta ttcatgaaag actttcaaa ggccaaggag       720 ggagttgtgg ctgctgctga gaaaaccaaa cagggtgtgg cagaagcagc aggaaagaca     780
aaagagggtg ttctctatgt aggctccaaa accaaggagg gagtggtgca tggtgtggca     840
acagtggctg agaagaccaa agagcaagtg acaaatgttg gaggagcagt ggtgacgggt     900
gtgacagcag tagcccagaa gacagtggag ggagcaggga gcattgcagc agccactggc     960
tttgtcaaaa aggaccagtt gggcaagaat gaagaaggag ccccacagga aggaattctg    1020
gaagatatgc ctgtggatcc tgacaatgag gcttatgaaa tgccttcttg aggaagggta    1080
tcaagactac gaacctgaag cctaa                                           1105
```

<210> SEQ ID NO 11
<211> LENGTH: 36
<212> TYPE: DNA
<213> ORGANISM: Artificial Sequence
<220> FEATURE:
<221> NAME/KEY: primer_bind
<222> LOCATION: (1)..(36)
<223> OTHER INFORMATION:

<400> SEQUENCE: 11

```
gcgctcgagc cagatctgcc atggatgtat tcatga                                36
```

<210> SEQ ID NO 12
<211> LENGTH: 36
<212> TYPE: DNA
<213> ORGANISM: Artificial Sequence
<220> FEATURE:
<221> NAME/KEY: primer_bind
<222> LOCATION: (1)..(36)
<223> OTHER INFORMATION:

```
<400> SEQUENCE: 12
gcgcaagctt gtcgacttag gcttcaggtt cgtagt                              36

<210> SEQ ID NO 13
<211> LENGTH: 37
<212> TYPE: DNA
<213> ORGANISM: Artificial Sequence
<220> FEATURE:
<221> NAME/KEY: primer_bind
<222> LOCATION: (1)..(37)
<223> OTHER INFORMATION:

<400> SEQUENCE: 13
gcgcaagctt gtcgacctat ttggtcttct cagccac                             37

<210> SEQ ID NO 14
<211> LENGTH: 28
<212> TYPE: DNA
<213> ORGANISM: Artificial Sequence
<220> FEATURE:
<221> NAME/KEY: primer_bind
<222> LOCATION: (1)..(28)
<223> OTHER INFORMATION:

<400> SEQUENCE: 14
gcgcagatct catatggagc aagtgaca                                       28

<210> SEQ ID NO 15
<211> LENGTH: 34
<212> TYPE: DNA
<213> ORGANISM: Artificial Sequence
<220> FEATURE:
<221> NAME/KEY: primer_bind
<222> LOCATION: (1)..(34)
<223> OTHER INFORMATION:

<400> SEQUENCE: 15
gcgcaagctt gtcgacctag acttagccag tggc                                34

<210> SEQ ID NO 16
<211> LENGTH: 40
<212> TYPE: DNA
<213> ORGANISM: Artificial Sequence
<220> FEATURE:
<221> NAME/KEY: primer_bind
<222> LOCATION: (1)..(40)
<223> OTHER INFORMATION:

<400> SEQUENCE: 16
gcgcggtacc gagatctgga tgaaaaagga ccagttgggc                          40

<210> SEQ ID NO 17
<211> LENGTH: 36
<212> TYPE: DNA
<213> ORGANISM: Artificial Sequence
<220> FEATURE:
<221> NAME/KEY: primer_bind
<222> LOCATION: (1)..(36)
<223> OTHER INFORMATION:

<400> SEQUENCE: 17
gcgcaagctt gtcgacttag gcttcaggtt cgtagt                              36

<210> SEQ ID NO 18
<211> LENGTH: 32
<212> TYPE: DNA
<213> ORGANISM: Artificial Sequence
```

```
<220> FEATURE:
<221> NAME/KEY: primer_bind
<222> LOCATION: (1)..(32)
<223> OTHER INFORMATION:

<400> SEQUENCE: 18
gcgcggtacc aaggaccagt tgggcaagaa tg                                    32

<210> SEQ ID NO 19
<211> LENGTH: 30
<212> TYPE: DNA
<213> ORGANISM: Artificial Sequence
<220> FEATURE:
<221> NAME/KEY: primer_bind
<222> LOCATION: (1)..(30)
<223> OTHER INFORMATION:

<400> SEQUENCE: 19
gcgcgtcgac ttaggcttca ggttcgtagt                                       30

<210> SEQ ID NO 20
<211> LENGTH: 48
<212> TYPE: DNA
<213> ORGANISM: Artificial Sequence
<220> FEATURE:
<221> NAME/KEY: primer_bind
<222> LOCATION: (1)..(48)
<223> OTHER INFORMATION:

<400> SEQUENCE: 20
gatccaatga agaaggagcc ccacaggaag gcattctgga agattaag                   48

<210> SEQ ID NO 21
<211> LENGTH: 48
<212> TYPE: DNA
<213> ORGANISM: Artificial Sequence
<220> FEATURE:
<221> NAME/KEY: primer_bind
<222> LOCATION: (1)..(48)
<223> OTHER INFORMATION:

<400> SEQUENCE: 21
aattcttaat cttccagaat gccttcctgt ggggctcctt cttcattg                   48

<210> SEQ ID NO 22
<211> LENGTH: 48
<212> TYPE: DNA
<213> ORGANISM: Artificial Sequence
<220> FEATURE:
<221> NAME/KEY: primer_bind
<222> LOCATION: (1)..(48)
<223> OTHER INFORMATION:

<400> SEQUENCE: 22
gatccgaaga tatgcctgta gatcctgaca atgaggctta tgaataag                   48

<210> SEQ ID NO 23
<211> LENGTH: 48
<212> TYPE: DNA
<213> ORGANISM: Artificial Sequence
<220> FEATURE:
<221> NAME/KEY: primer_bind
<222> LOCATION: (1)..(48)
<223> OTHER INFORMATION:

<400> SEQUENCE: 23
aattcttatt cataagcctc attgtcagga tctacaggca tatcttcg                   48
```

<210> SEQ ID NO 24
<211> LENGTH: 75
<212> TYPE: DNA
<213> ORGANISM: Artificial Sequence
<220> FEATURE:
<221> NAME/KEY: primer_bind
<222> LOCATION: (1)..(75)
<223> OTHER INFORMATION:

<400> SEQUENCE: 24
gatccgatcc tgacaatgag gcttatgaaa tgccttctga ggaagggtat caagactacg    60
aacctgaagc ctaag                                                    75

<210> SEQ ID NO 25
<211> LENGTH: 75
<212> TYPE: DNA
<213> ORGANISM: Artificial Sequence
<220> FEATURE:
<221> NAME/KEY: primer_bind
<222> LOCATION: (1)..(75)
<223> OTHER INFORMATION:

<400> SEQUENCE: 25
aattcttagg cttcaggttc gtagtcttga tacccttcct cagaaggcat ttcataagcc    60
tcattgtcag gatcg                                                    75

<210> SEQ ID NO 26
<211> LENGTH: 42
<212> TYPE: DNA
<213> ORGANISM: Artificial Sequence
<220> FEATURE:
<221> NAME/KEY: primer_bind
<222> LOCATION: (1)..(42)
<223> OTHER INFORMATION:

<400> SEQUENCE: 26
gatccgagga agggtatcaa gactacgaac ctgaagccta ag                      42

<210> SEQ ID NO 27
<211> LENGTH: 42
<212> TYPE: DNA
<213> ORGANISM: Artificial Sequence
<220> FEATURE:
<221> NAME/KEY: primer_bind
<222> LOCATION: (1)..(42)
<223> OTHER INFORMATION:

<400> SEQUENCE: 27
aattcttagg cttcaggttc gtagtcttga tacccttcct cg                      42

<210> SEQ ID NO 28
<211> LENGTH: 28
<212> TYPE: DNA
<213> ORGANISM: Artificial Sequence
<220> FEATURE:
<221> NAME/KEY: primer_bind
<222> LOCATION: (1)..(28)
<223> OTHER INFORMATION:

<400> SEQUENCE: 28
agctaaggat ccaagaggga ggaattcc                                      28

<210> SEQ ID NO 29
<211> LENGTH: 30
<212> TYPE: DNA
<213> ORGANISM: Artificial Sequence

```
<220> FEATURE:
<221> NAME/KEY: primer_bind
<222> LOCATION: (1)..(30)
<223> OTHER INFORMATION:

<400> SEQUENCE: 29
aagtaactcg agctacgcct ctggctcata                              30

<210> SEQ ID NO 30
<211> LENGTH: 28
<212> TYPE: DNA
<213> ORGANISM: Artificial Sequence
<220> FEATURE:
<221> NAME/KEY: primer_bind
<222> LOCATION: (1)..(28)
<223> OTHER INFORMATION:

<400> SEQUENCE: 30
aagaatggat cccgcaagga ggacttga                                28

<210> SEQ ID NO 31
<211> LENGTH: 29
<212> TYPE: DNA
<213> ORGANISM: Artificial Sequence
<220> FEATURE:
<221> NAME/KEY: primer_bind
<222> LOCATION: (1)..(29)
<223> OTHER INFORMATION:

<400> SEQUENCE: 31
aatagcgaat tcctagtctc ccccactct                               29

<210> SEQ ID NO 32
<211> LENGTH: 23
<212> TYPE: DNA
<213> ORGANISM: Artificial Sequence
<220> FEATURE:
<221> NAME/KEY: primer_bind
<222> LOCATION: (1)..(23)
<223> OTHER INFORMATION:

<400> SEQUENCE: 32
gatccgaaga agaagaagaa taa                                     23

<210> SEQ ID NO 33
<211> LENGTH: 24
<212> TYPE: DNA
<213> ORGANISM: Artificial Sequence
<220> FEATURE:
<221> NAME/KEY: primer_bind
<222> LOCATION: (1)..(24)
<223> OTHER INFORMATION:

<400> SEQUENCE: 33
aattcttatt cttcttcttc ttcg                                    24

<210> SEQ ID NO 34
<211> LENGTH: 39
<212> TYPE: DNA
<213> ORGANISM: Artificial Sequence
<220> FEATURE:
<221> NAME/KEY: primer_bind
<222> LOCATION: (1)..(39)
<223> OTHER INFORMATION:

<400> SEQUENCE: 34
gatccgaaga agaagaagaa gaagaagaag aagaataag                    39
```

-continued

```
<210> SEQ ID NO 35
<211> LENGTH: 39
<212> TYPE: DNA
<213> ORGANISM: Artificial Sequence
<220> FEATURE:
<221> NAME/KEY: primer_bind
<222> LOCATION: (1)..(39)
<223> OTHER INFORMATION:

<400> SEQUENCE: 35
aattcttatt cttcttcttc ttcttcttct tcttcttcg                              39

<210> SEQ ID NO 36
<211> LENGTH: 5
<212> TYPE: PRT
<213> ORGANISM: Artificial Sequence
<220> FEATURE:
<221> NAME/KEY: PEPTIDE
<222> LOCATION: (1)..(5)
<223> OTHER INFORMATION:

<400> SEQUENCE: 36

Glu Glu Glu Glu Glu
1               5

<210> SEQ ID NO 37
<211> LENGTH: 10
<212> TYPE: PRT
<213> ORGANISM: Artificial Sequence
<220> FEATURE:
<221> NAME/KEY: PEPTIDE
<222> LOCATION: (1)..(10)
<223> OTHER INFORMATION:

<400> SEQUENCE: 37

Glu Glu Glu Glu Glu Glu Glu Glu Glu Glu
1               5                   10
```